United States Patent [19]

Lee et al.

[11] Patent Number: 5,776,936
[45] Date of Patent: Jul. 7, 1998

[54] MARCFORTINE/PARAHERQUAMIDE DERIVATIVES USEFUL AS ANTIPARASITIC AGENTS

[75] Inventors: Byung H. Lee, Kalamazoo; Stephen J. Nelson, Climax, both of Mich.

[73] Assignee: Pharmacia & Upjohn Company, Kalamazoo, Mich.

[21] Appl. No.: 256,111

[22] PCT Filed: Nov. 13, 1992

[86] PCT No.: PCT/US92/09483

§ 371 Date: May 19, 1994

§ 102(e) Date: May 19, 1994

[87] PCT Pub. No.: WO93/10120

PCT Pub. Date: May 27, 1993

[51] Int. Cl.$^6$ .................. C07D 491/22; A01N 43/90; C12P 17/18; A61K 31/495
[52] U.S. Cl. .................. 514/250; 544/229; 544/230; 435/118
[58] Field of Search .................. 544/230, 229; 514/250; 435/118

[56] References Cited

FOREIGN PATENT DOCUMENTS 0 354 615   8/1989   European Pat. Off. ...... C07D 491/22
92/00300   1/1992   WIPO ...... C07D 491/22

OTHER PUBLICATIONS

Blizzard, Timothy A; Margiano, Gaye; Mrozik, Helmut; Schaeffer, James M; Fisher, Michael H; Chemical Modification of Paraherquamide. 4. 1-N-Substituted Analogs, Tetrahedron Letters, vol. 32, No. 22, pp. 2441-2444, 1991.
Blizzard, Timothy A; Marino, Gaye; Mrozik, Helmut; Fisher, Michael H; Hoogsteen, Karst; Springer, James P; Chemical Modification of Paraherquamide. 1. Unusual Reactions and Absolute Stereochemistry, Journal Org. Chem. 1989, 54, 2657-2663.

*Primary Examiner*—Robert T. Bond
*Attorney, Agent, or Firm*—William G. Jameson

[57] ABSTRACT

There are disclosed 18-thiomarcfortine derivatives of the natural products marcfortine A, B and C, C-18 thioparaherquamide and derivatives thereof, novel N-1 marcfortines A, B, and C and derivatives thereof, novel N-1 paraherquamide and derivatives thereof usefull in the treatment and prevention of helninth and arthropod infections of animals and plants.

Any inquiry concerning this communication or earlier communications from the examiner should be directed to Examiner Robert T. Bond whose telephone number is (703)308-4711. The examiner can normally be reached on Monday through Friday from 8:00 AM to 4:30 PM.

19 Claims, No Drawings

MARCFORTINE/PARAHERQUAMIDE DERIVATIVES USEFUL AS ANTIPARASITIC AGENTS

BACKGROUND OF THE INVENTION

The marcfortines are known compounds and are disclosed by Polonsky et al. in Journal of the Chemical Society Chemical Communications 1980 601–602 (Marcfortine A) and Tetrahedron Letters 1981 22 1977–1980 (Marcfortines B and C). The compounds are fungal metabolites of *Penicillium roqueforti*. The marcfortines are structurally related to the paraherquamides which are also known compounds. The paraherquamides are disclosed by Yamazaki et al. in Tetrahedron Letters 1981 22 135–136, and by Blanchflower et al., Journal of Antibioties, 1991, 44, 492–497. U.S. Pat. Nos. 4,866,060 and 4,923,867 disclose the use of the marcfortines A, B, and C, and certain derivatives thereof as useful for the treatment and prevention of parasitic diseases in animals.

Paraherquamide has the following structure:

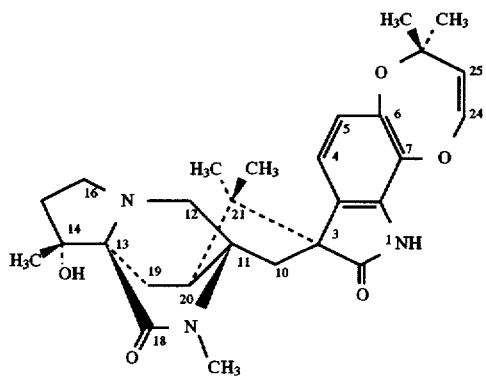

Marcfortine A has the following structure:

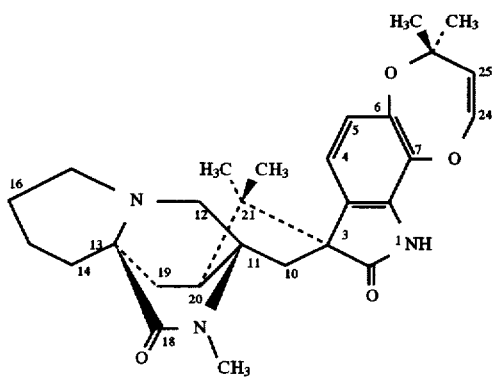

Marcfortine B has the following structure:

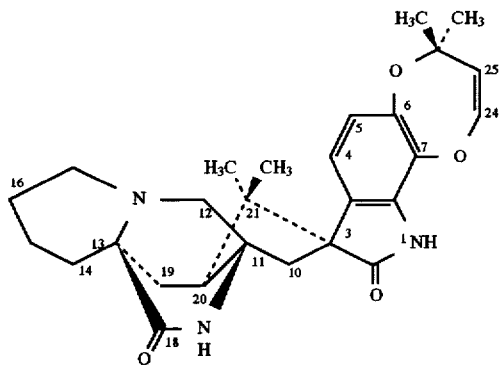

Marfortine C has the following structure:

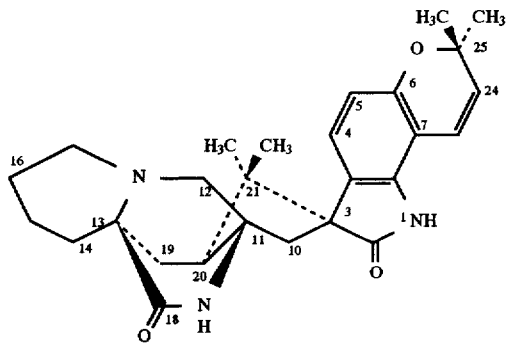

WO 91/09961 (published 11, Jul. 1991) discloses various derivatives of marcfortine and paraherquamide, and N(12) oxides thereof, well as the production the production of VM 29919 (paraherquamide) and VM 55596 (the N(12)oxide of paraherquamide) inter alia from Penicillium Sp. IMI 332995.

U.S. Pat. No. 4,873,247 discloses derivatives of paraherquamide and a strain of *Penicillium charlessi* MF 5123 (ATCC 20841) for the production of paraherquamide. U.S. Pat. No. 4,978,656 (as well as EP 390532-A, EP-301742-A) discloses various synthetic derivatives of paraherquamide as well as the production of paraherquamide from *Penicillium chariessi* MF 5123 (ATCC 20841).

Paraherquamide is a compound produced under certain conditions by the fungal organism *Penicllium paraherquei*. WO 92/00300 (published 9 Jan. 1992) discloses the synthesis paraherquamide related compounds produced from *Penicillium paraherquei*, deposited at the C.A.B. International Mycological Institute, Ferry Lane, Kew, London, under deposit number CMI 68220.

SUMMARY OF THE INVENTION

This invention is concerned with the synthesis of C-18 thiomarcfortine A, B, and C and derivatives thereof, C-18 thioparaherquamide and derivatives thereof, novel N-1 marcfortines A, B, and C and derivatives thereof, novel N-1 paraherquamide and derivatives thereof, and the use of these compounds as antiparasitic agents. Thus it is an object of this invention to describe these thiomarcfortine, thioparaherquamide, marcfortine and paraherquamide derivatives. A further objective of this invention is to describe processes for the preparation of these compounds.

A still further objective is to describe the use of the instant compounds as antiparasitic agents in the treatment and prevention of parasitic diseases. A still further object is to describe compositions for the treatment of parasitic diseases which contain the novel compounds of this invention as the active ingredient thereof. Further objectives will become apparent from a reading of the following description.

DESCRIPTION OF THE INVENTION

The compounds of the instant invention are represented by Formula I:

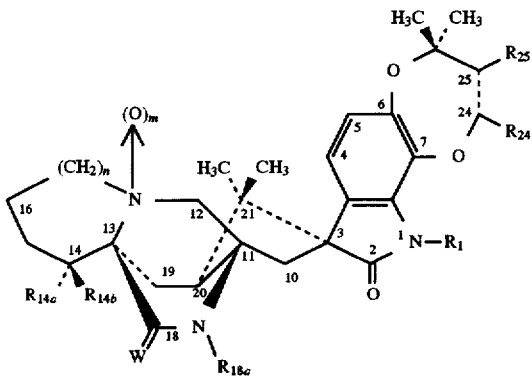

wherein:

n is 0 or 1;

$R_{14a}$ and $R_{14b}$, being the same or different, are selected from hydrogen, hydroxy, $C_1$–$C_6$ alkyl, $C_1$–$C_6$ alkoxy, $C_1$–$C_6$ alkenyl, $C_1$–$C_6$ alkenyl-$C_1$–$C_6$ alkoxy, $C_1$–$C_6$ alkynyl-$C_1$–$C_6$ alkoxy, $C_1$–$C_6$alkylsilyloxy, diphenylphosphoryloxy and halogen, or $R_{14a}$ and $R_{14b}$ together form the epoxide or $=CH_2$, with the provisio that when n is 1, then $R_{14a}$ and $R_{14b}$ are both hydrogen;

m is 0 or 1 (preferably 0);

W is O or S;

when W is S, $R_1$ is hydrogen, $C_1$–$C_7$ alkyl, cyclo $C_3$–$C_8$alkyl, benzyl, $C_2$–$C_7$ alkanoyl (—C(O)$C_1$–$C_6$alkyl) {optionally substituted with carboxy (—COOH), $C_1$–$C_7$ alkanoyl, carbo $C_1$–$C_7$alkoxy (—C(O)O$C_1$–$C_7$alkyl), —NR$_4$R$_5$, aminocarbonyl (—C(O)NR$_4$R$_5$)}, $C_{10}$–$C_{24}$alkanoyl (—C(O)$C_9$–$C_{23}$alkyl, cyclo $C_3$–$C_8$alkanoyl {optionally substituted with carboxy, $C_1$–$C_7$ alkanoyl, carbo$C_1$–$C_7$alkoxy, —NR$_4$R$_5$, aminocarbonyl}, alkanoyloxymethylene (—CH$_2$OC(O)—$C_2$–$C_7$alkyl), benzoyloxymethylene (—CH$_2$OC(O)phenyl) {optionally substituted with 1 or 2 groups selected from halogen, $C_1$–$C_4$ alkyl, halo$C_1$–$C_7$alkyl, nitro, cyano and $C_1$–$C_7$alkoxy}, $C_{10}$–$C_{24}$alkenoyl (—C(O)$C_9$–$C_{23}$alkenyl), benzenesulfonyl (—SO$_2$phenyl) {optionally substituted with 1 or 2 groups selected from halogen, $C_1$–$C_4$ alkyl, halo$C_1$–$C_7$alkyl, nitro, cyano and $C_1$–$C_7$alkoxy}, di($C_1$–$C_4$alkyl)aminocarbonyl (—C(O)N($C_1$–$C_4$alkyl)$_2$), di($C_1$–$C_4$alkyl) aminothiocarbonyl (—C(S)N ($C_1$–$C_4$alkyl)$_2$), $C_1$–$C_7$ alkoxycarbonyl, phenoxycarbonyl {optionally substituted with 1 or 2 groups selected from halogen, $C_1$–$C_4$ alkyl, halo$C_1$–$C_7$alkyl, nitro, cyano and $C_1$–$C_7$alkoxy}, —C(O) NR'$_4$R'$_5$, —P(=X)(R$_2$)(R$_3$), —SR$_6$—SO$_2$NR$_4$R5, benzoyl substituted at the 3 or 4 position with —CH$_2$NR$_4$R$_5$, or 2-tetrahydrofuran or bicyclo$C_8$–$C_{12}$alkanoyl;

when W is O; $R_1$ is selected from the group consisting of:
(a) $C_2$–$C_7$ alkanoyl substituted with carboxy (—COOH), $C_1$–$C_7$alkanoyl, carbo$C_1$–$C_7$alkoxy (—C(O) O$C_1$–$C_7$alkyl), —NR$_4$R$_5$, aminocarbonyl (—C(O) NR$_4$R$_5$);

(b) cyclo $C_3$–$C_8$alkanoyl optionally substituted with carboxy, $C_1$–$C_7$alkanoyl, carbo$C_1$–$C_7$alkoxy. —NR$_4$R$_5$, aminocarbonyl;

(c) alkanoyloxymethylene (—CH$_2$OC(O)—$C_2$–$C_7$alkyl);

(d) benzoyloxymethlene (—CH$_2$OC(O)phenyl) substituted with 1 or 2 groups selected from halogen, $C_1$–$C_4$ alkyl, halo$C_1$–$C_7$alkyl, nitro, cyano and $C_1$–$C_7$alkoxy;

(e) phenoxycarbonyl substituted with 1 or 2 groups selected from halogen, $C_1$–$C_4$ alkyl, halo$C_1$–$C_7$alkyl, nitro, cyano and $C_1$–$C_7$alkoxy;

(f) —C(O)NR'$_4$R'$_5$;

(g) —P(=X)(R$_2$(R$_3$);

(h) —SR$_6$;

(i) $C_{10}$–$C_{24}$alkanoyl (—C(O)$C_{10-C24}$alkyl);

(j) $C_{10}$–$C_{24}$alkenoyl (—C(O)$_9$–$C_{23}$alkenyl); or (k) 2-tetrahydrofuran;

$R_4$ and $R_5$, being the same or different, are selected from hydrogen, $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated or unsaturated heterocyclic amine ring;

R'$_4$ and R'$_5$, being the same or different, are selected from $C_1$–$C_7$alkyl, cyclo($C_3$–$C_8$)alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated heterocyclic amine ring optionally containing 1 or 2 additional heteroatoms selected from N, O or S;

X is O or S;

$R_2$ and $R_3$, being the same or different, are selected from $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxyl}, $C_1$–$C_7$ alkoxy, thio($C_1$–$C_7$) alkoxy, phenoxy, thiophenoxy, —NR$_7$R$_8$ {where $R_7$ and $R_8$, being the same or different, are selected from H, $C_1$–$C_7$ alkyl or taken together with N, form a saturated heterocyclic ring}, or taken together with P form a 4- to 7-membered heterocyclic ring;

$R_6$ is $C_1$–$C_7$ alkyl, halo$C_1$–$C_7$alkyl, carbo$C_1$–$C_7$alkoxy, —NR$_9$R$_{10}$ where $R_9$ and $R_{10}$, being the same or different, are $C_1$–$C_7$ alkyl or phenyl (optionally substituted with 1 or 2 groups selected from halo, lower alkyl, halo$C_1$–$C_7$alkyl, nitro, cyano, $C_1$–$C_7$ alkoxy);

$R_{24}$ is hydrogen, halogen or $C_1$–$C_7$ alkoxy;

$R_{25}$ is hydrogen or halogen;

$R_{18a}$ is hydrogen, $C_1$–$C_7$ alkyl, $C_2$–$C_8$alkoxyalkyl, $C_2$–$C_8$ alkenyl, $C_2$–$C_8$ alkynyl or benzyl;

the broken line between carbons 24 and 25 represents a single or double bond.

The compounds of this invention include pharmaceutically acceptable salts thereof as well as 12a-N-oxides thereof.

Another aspect of this invention are 10,10"-(1,4-dicarbonylpiperazine) bis(6',7',8',9',10',10'a-hexahydro-1',1',4,4,12'-pentamethyl)-[2'S-[2'.alpha., 3'a.alpha., 9'a.alpha.,10(2'''R*, 3'''aS*9'''aS*, 10'''aR*) 10'a.beta]]-Spiro[4H,8H-[1,4]dioxepino[2,3-g]indole-8,2' (3'H)-[1H,4H-3a,9a](iminomethano) cyclopenta[b] quinolizin]-9,11'(10H)-dione—Cpd #12O), and 10,10"-(1,4-dioxo-2-butene)bis(6',7',8',9',10',10'a-hexahydro-1',1',4,4,12'-pentamethyl)-[2'S-[2'.alpha., 3'a.alpha,9'a.alpha,10(2'''aR*,3'''aS*9'''aS,10'''aR*), 10'a.beta]]-Spiro[4H,8H-[1,4]dioxepino[2,3-g]indole-8,2' (3'H)-[1H,4H-3a,9a](imino methano)cyclopenta[b]

quinolizin]-9,11'(10H)-dione, Cpd #12T), which can be used in the same manner as compounds of Formula I.

Another aspect of this invention provides an 18-thiomarcfortine or derivatives of Formula II:

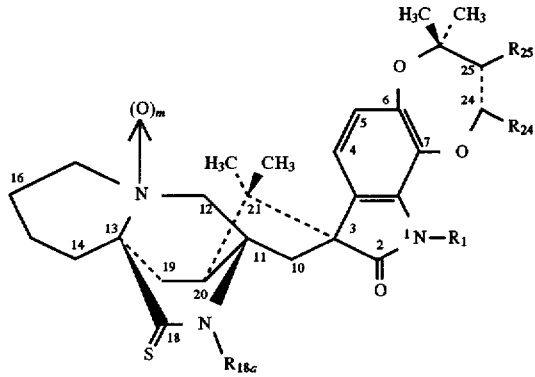

wherein:

m is 0 or 1 (preferably 0);

$R_1$ is hydrogen, $C_1$–$C_7$ alkyl, cyclo $C_3$–$C_8$alkyl, benzyl, $C_2$–$C_7$ alkanoyl (—C(O)($C_1$–$C_6$alkyl) {optionally substituted with carboxy (—COOH), $C_1$–$C_7$ alkanoyl, carbo $C_1$–$C_7$alkoxy (—C(O)O$C_1$–$C_7$alkyl), —$NR_4R_5$, aminocarbonyl (-C(O)$NR_4R_5$)}, $C_{10}$–$C_{24}$alkanoyl (—C(O)$C_9$–$C_{23}$-alkyl, cyclo $C_3$–$C_8$alkanoyl {optionally substituted with carboxy, $C_1$–$C_7$ alkanoyl, carbo$C_1$–$C_7$alkoxy, —$NR_4R_5$, aminocarbonyl}, alkanoyloxymethylene (—$CH_2$OC(O)—$C_2$—$C_7$alkyl), benzoyloxymethlene (—$CH_2$OC(O)phenyl) {optionally substituted with 1 or 2 groups selected from halogen, $C_1$–$C_4$ alkyl, halo$C_1$–$C_7$alkyl, nitro, cyano and $C_1$–$C_7$alkoxy}, $C_{10}$–$C_{24}$alkenoyl (—C(O)$C_9$–$C_{23}$alkenyl), benzenesulfonyl (—$SO_2$phenyl) {optionally substituted with 1 or 2 groups selected from halogen, $C_1$–$C_4$ alkyl, halo$C_1$–$C_7$alkyl, nitro, cyano and $C_1$–$C_7$alkoxy}, di($C_{10}$–$C_4$ alkyl)aminocarbonyl (—C(O)N($C_1$–$C_4$alkyl)$_2$), di($C_1$–$C_4$alkyl)aminothiocarbonyl (—C(S)N($C_1$–$C_4$alkyl)$_2$), $C_1$–$C_7$ alkoxycarbonyl, phenoxycarbonyl {optionally substituted with 1 or 2 groups selected from halogen, $C_1$–$C_4$ alkyl, halo$C_1$–$C_7$alkyl, nitro, cyano and $C_1$–$C_7$alkoxy}, —C(O)$NR'_4R'_5$, —P(=X)($R_2$) ($R_3$), —$SR_6$, —$SO_2NR_4R_5$, benzoyl substituted at the 3 or 4 position with —$CH_2NR_4R_5$, 2-tetrahydrofuran, or bicyclo$C_8$–$C_{12}$alkanoyl;

$R_4$ and $R_5$, being the same or different, are selected from hydrogen, $C_1$–$C_7$ alkyl, phenyl {optionally substituted with 1 or 2 groups selected from halogen, $C_1$–$C_4$ alkyl, halo $C_1$–$C_7$ alkyl, nitro, cyano and $C_1$–$C_7$alkoxy} or when taken together with N, form a saturated or unsaturated heterocyclic amine ring;

$R'_4$ and $R'_5$, being the same or different, are selected from $C_1$–$C_7$ alkyl, cyclo($C_3$–$C_8$)alkyl, phenyl {optionally substituted with 1 or 2 groups selected from halogen, $C_1$–$C_4$ alkyl, halo$C_1$–$C_7$alkyl, nitro, cyano and $C_4$–$C_7$alkoxy} or when taken together with N, form a saturated heterocyclic amine ring optionally containing 1 or 2 additional heteroatoms selected from N, O or S;

X is O or S;

$R_2$ and $R_3$, being the same or different, are selected from $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy}, $C_1$–$C_7$ alkoxy, phenoxy, thiophenoxy, —$NR_7R_8$ {where $R_7$ and $R_8$, being the same or different, are selected from H, $C_1$–$C_7$ alkyl or taken together with N, form a saturated heterocyclic ring}, or taken together with P form a 4- to 7-membered heterocyclic ring;

$R_6$ is $C_1$–$C_7$ alkyl, halo$C_1$–$C_7$alkyl, carbo$C_1$–$C_7$alkoxy, —$NR_9R_{10}$ where $R_9$ and $R_{10}$, being the same or different, are $C_1$–$C_7$ alkyl or phenyl (optionally substituted with 1 or 2 groups selected from halo, lower alkyl, halo$C_1$–$C_7$alkyl, nitro, cyano, $C_1$–$C_7$ alkoxy);

$R_{24}$ is hydrogen, halogen or $C_1$–$C_7$ alkoxy;

$R_{25}$ is hydrogen or halogen;

$R_{18a}$ is hydrogen, $C_1$–$C_7$ alkyl, $C_2$–$C_8$ alkoxyalkyl, $C_2$–$C_8$ alkenyl, $C_2$–$C_8$ alkynyl or benzyl; the broken line between carbons 24 and 25 represents a single or double bond.

Another aspect of this invention provides an 18-thioparaherquamide or derivatives of Formula III:

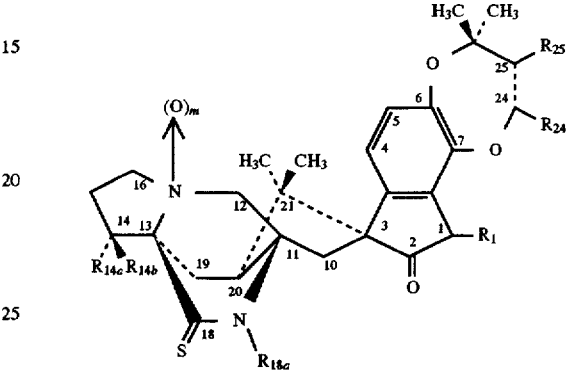

wherein:

m is 0 or 1 (preferably 0);

$R_1$ is hydrogen, $C_1$–$C_7$ alkyl, cyclo $C_3$–$C_8$alkyl, benzyl, $C_2$–$C_7$ alkanoyl (—C(O)$C_1$—$C_6$alkyl) {optionally substituted with carboxy (—COOH), $C_1$–$C_7$ alkanoyl, carbo $C_1$–$C_7$alkoxy (—C(O)O$C_1$–$C_7$alkyl), —$NR_4R_5$, aminocarbonyl (—C(O)$NR_4R_5$)}, $C_{10}$–$C_{24}$alkanoyl (—C(O) $C_9$–$C_{23}$alkyl, cyclo $C_3$–$C_8$alkanoyl {optionally substituted with carboxy, $C_1$–$C_7$ alkanoyl, carbo$C_1$–$C_7$alkoxy, —$NR_4R_5$, aminocarbonyl}, alkanoyloxymethylene (—$CH_2$OC(O)—$C_2$-$C_7$alkyl), benzoyloxymethlene (—$CH_2$OC(O)phenyl) {optionally substituted with 1 or 2 groups selected from halogen, $C_1$–$C_4$ alkyl, halo$C_1$–$C_7$alkyl, nitro, cyano and $C_1$–$C_7$alkoxy}, $C_{10}$–$C_{24}$alkenoyl (—C(O) $C_9$–$C_{23}$alkenyl), benzenesulfonyl (—$SO_2$phenyl) {optionally substituted with 1 or 2 groups selected from halogen, $C_1$–$C_4$ alkyl, halo$C_1$–$C_7$alkyl, nitro, cyano and $C_1$–$C_7$alkoxy}, di($C_1$–$C_4$alkyl)aminocarbonyl (—C(O)N ($C_1$–$C_4$alkyl)$_2$), di($C_1$–$C_4$alkyl)aminothiocarbonyl (—C(S)N ($C_1$–$C_4$alkyl)$_2$), $C_1$–$C_7$ alkoxycarbonyl, phenoxycarbonyl {optionally substituted with 1 or 2 groups selected from halogen, $C_1$–$C_4$ alkyl, halo$C_1$–$C_7$alkyl, nitro, cyano and $C_1$–$C_7$alkoxy}, —C(O)$NR'_4R'_5$, —P(=X)($R_2$)($R_3$), —$SR_6$, —$SO_2NR_4R5$, benzoyl substituted at the 3 or 4 position with —$CH_2NR_4R_5$, 2-tetrahydrofuran, or bicyclo$C_8$–$C_{12}$alkanoyl;

$R_4$ and $R_5$, being the same or different, are selected from hydrogen, $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated or unsaturated heterocyclic amine ring;

$R'_4$ and $R'_5$, being the same or different, are selected from $C_1$–$C_7$ alkyl, cyclo($C_3$–$C_8$)alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated heterocyclic amine ring optionally containing 1 or 2 additional heteroatoms selected from N, O or S;

X is O or S;

$R_2$ and $R_3$, being the same or different, are selected from $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy}, $C_1$–$C_7$ alkoxy, thio($C_1$–$C_7$) alkoxy, phenoxy, thiophenoxy, —$NR_7R_8$ {where $R_7$ and $R_8$, being the same or different, are selected from H, $C_1$–$C_7$ alkyl or taken together with N, form a saturated heterocyclic ring}, or taken together with P form a 4- to 7-membered heterocyclic ring;

$R_6$ is $C_1$–$C_7$ alkyl, halo$C_1$–$C_7$alkyl, carbo$C_1$–$C_7$alkoxy, —$NR_9R_{10}$ where $R_9$ and $R_{10}$, being the same or different, are $C_1$–$C_7$ alkyl or phenyl (optionally substituted with 1 or 2 groups selected from halo, lower alkyl, halo$C_1$–$C_7$alkyl, nitro, cyano, $C_1$–$C_7$ alkoxy);

$R_{24}$ is hydrogen, halogen or $C_1$–$C_7$ alkoxy;

$R_{25}$ is hydrogen or halogen;

$R_{14a}$ and $R_{14b}$, being the same or different, are selected from hydrogen, hydroxy, $C_1$–$C_6$ alkyl, $C_1$–$C_6$ alkoxy, $C_1$–$C_6$ alkenyl, $C_1$–$C_6$ alkenyl-$C_1$–$C_6$ alkoxy, $C_1$–$C_6$ alkynyl-$C_1$–$C_6$ alkoxy, $C_1$–$C_6$ alkynoyloxy, poly $C_1$–$C_6$ alkoxy-$C_1$–$C_6$ alkoxy, phenyl, phenyl-$C_1$–$C_6$ alkyl, tri-$C_1$–$C_6$ alkylsilyloxy, diphenylphosphoryloxy and halogen, or $R_{14a}$ and $R_{14b}$ together form the epoxide or =$CH_2$;

$R_{18a}$ is hydrogen, $C_1$–$C_7$ alkyl, $C_2$–$C_8$ alkoxyalkyl, $C_2$–$C_8$ alkenyl, $C_2$–$C_8$ alkynyl or benzyl; the broken line between carbons 24 and 25 represents a single or double bond.

Another aspect of this invention provides novel N-1 marcfortine or derivatives of Formula IV:

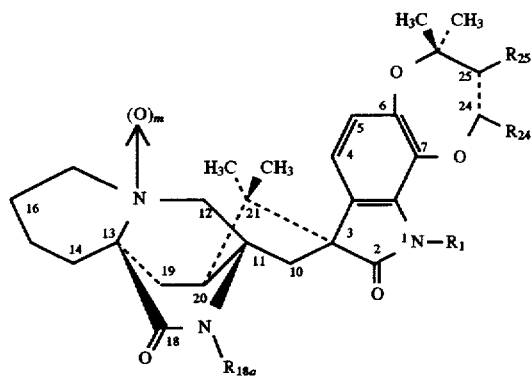

wherein:

m is 0 or 1 (preferably 0);

$R_1$ is selected from the group consisting of:

(a) $C_2$–$C_7$ alkanoyl substituted with carboxy (—COOH), $C_1$–$C_7$ alkanoyl, carbo$C_1$–$C_7$alkoxy (—C(O)O$C_1$–$C_7$alkyl), —$NR_4R_5$, aminocarbonyl (—C(O)$NR_4R_5$);

(b) cyclo $C_3$–$C_8$alkanoyl optionally substituted with carboxy, $C_1$–$C_7$ alkanoyl, carbo$C_1$–$C_7$alkoxy, —$NR_4R_5$, aminocarbonyl;

(c) alkanoyloxymethylene (—$CH_2$OC(O)-$C_2$–$C_7$alkyl);

(d) benzoyloxymethlene (—$CH_2$OC(O)phenyl) substituted with 1 or 2 groups selected from halogen, $C_1$–$C_4$ alkyl, halo$C_1$–$C_7$alkyl, nitro, cyano and $C_1$–$C_7$alkoxy;

(e) phenoxycarbonyl substituted with 1 or 2 groups selected from halogen, $C_1$–$C_4$ alkyl, halo$C_1$–$C_7$alkyl, nitro, cyano and $C_1$–$C_7$alkoxy;

(f) —C(O)$NR'_4R'_5$;

(g) —P(=X)($R_2$)($R_3$);

(h) —$SR_6$;

(i) $C_9$–$C_{23}$alkanoyl (—C(O)$C_{10}$–$C_{24}$alkyl);

(j) $C_{10}$–$C_{24}$alkenoyl (—C(O)$C_9$–$_{23}$alkenyl); or (k) 2-tetrahydrofuran;

$R_4$ and $R_5$, being the same or different, are selected from hydrogen, $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated or unsaturated heterocyclic amine ring;

$R'_4$ and $R'_5$, being the same or different, are selected from $C_1$–$C_7$ alkyl, cyclo($C_3$–$C_8$)alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated heterocyclic amine ring optionally containing 1 or 2 additional heteroatoms selected from N, O or S;

X is O or S;

$R_2$ and $R_3$, being the same or different, are selected from $C_1$–$C_7$ alkyl phenyl {optionally substituted with 1 or 2 groups selected from halogen, $C_1$–$C_4$ alkyl, halo$C_1$–$C_7$alkyl, nitro, cyano and $C_1$–$C_7$alkoxy}, $C_1$–$C_7$ alkoxy, thio($C_1$–$C_7$) alkoxy, phenoxy, thiophenoxy, —$NR_7R_8$ {where $R_7$ and $R_8$, being the same or different, are selected from H, $C_1$–$C_7$ alkyl or taken together with N, form a saturated heterocyclic ring}, or taken together with P form a 4- to 7-membered heterocyclic ring;

$R_6$ is $C_1$–$C_7$ alkyl, halo$C_1$–$C_7$alkyl, carbo$C_1$–$C_7$alkoxy, —$NR_9R_{10}$ where $R_9$ and $R_{10}$, being the same or different, are $C_1$–$C_7$ alkyl or phenyl (optionally substituted with 1 or 2 groups selected from halo, lower alkyl, halo$C_1$–$C_7$alkyl, nitro, cyano, $C_1$–$C_7$ alkoxy);

$R_{24}$ is hydrogen, halogen or $C_1$–$C_7$ alkoxy;

$R_{25}$ is hydrogen or halogen;

$R_{18a}$ is hydrogen, $C_1$–$C_7$ alkyl, $C_2$–$C_8$ alkoxyalkyl, $C_2$–$C_8$ alkenyl, $C_2$–$C_8$ alkynyl or benzyl;

the broken line between carbons 24 and 25 represents a single or double bond.

Another aspect of this invention provides novel N-1 paraherquamide or derivatives of Formula V:

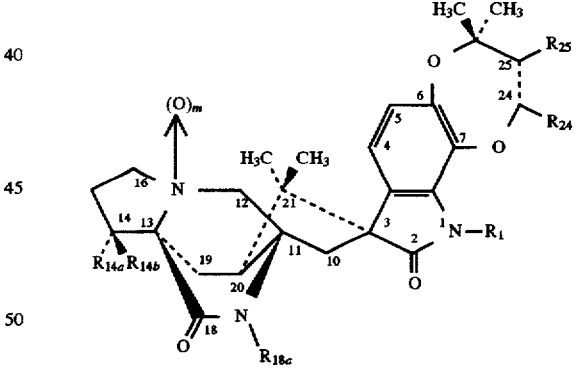

wherein:

m is 0 or 1 (preferably 0);

$R_1$ is selected from the group consisting of:

(a) $C_2$–$C_7$ alkanoyl substituted with carboxy (—COOH), $C_1$–$C_7$ alkanoyl, carbo$C_1$–$C_7$alkoxy (—C(O)O$C_1$–$C_7$alkyl), —$NR_4R_5$, aminocarbonyl (—C(O)$NR_4R_5$);

(b) cyclo $C_3$–$C_8$alkanoyl optionally substituted with carboxy, $C_1$–$C_7$ alkanoyl, carbo$C_1$–$C_7$alkoxy, —$NR_4R_5$, aminocarbonyl;

(c) alkanoyloxymethylene (—$CH_2$OC(O)—$C_2$–$C_7$alkyl);

(d) benzoyloxymethiene (—$CH_2$OC(O)phenyl) substituted with 1 or 2 groups selected from halogen, $C_1$–$C_4$ alkyl, halo$C_1$–$C_7$alkyl, nitro, cyano and $C_1$–$C_7$alkoxy;

(e) phenoxycarbonyl substituted with 1 or 2 groups selected from halogen, $C_1$–$C_4$ alkyl, halo$C_1$–$C_7$alkyl, nitro, cyano and $C_1$–$C_7$alkoxy;

(f) —C(O)NR'$_4$R'$_5$;

(g) —P(=X)(R$_2$)(R$_3$);

(h) —SR$_6$;

(i) $C_9$–$C_{23}$alkanoyl (—C(O)$C_{10}$–$C_{24}$alkyl);

(j) $C_{10}$–$C_{24}$alkenoyl (—C(O)$C_9$–$C_{23}$alkenyl); or (k) 2-tetrahydrofuran;

R$_4$ and R$_5$, being the same or different, are selected from hydrogen, $C_1$–$C_7$ alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated or unsaturated heterocyclic amine ring;

R'$_4$ and R'$_5$, being the same or different, are selected from $C_1$–$C_7$ alkyl, cyclo($C_3$–$C_8$)alkyl, phenyl {optionally substituted with 1 or 2 groups selected from halogen, $C_1$–$C_4$ alkyl, halo$C_1$–$C_7$alkyl, nitro, cyano and $C_1$–$C_7$alkoxy} or when taken together with N, form a saturated heterocyclic amine ring optionally containing 1 or 2 additional heteroatoms selected from N, O or S;

X is O or S;

R$_2$ and R$_3$, being the same or different, are selected from $C_1$–$C_7$ alkyl, phenyl (optionally substituted with 1 or 2 groups selected from halogen, $C_1$–$C_4$ alkyl, halo$C_1$–$C_7$alkyl, nitro, cyano and $C_1$–$C_7$alkoxyl, $C_1$–$C$, alkoxy, thio($C_1$–$C_7$) alkoxy, phenoxy, thiophenoxy, —NR$_7$R$_8$ {where R$_7$ and R$_8$, being the same or different, are selected from H, $C_1$–$C_7$ alkyl or taken together with N, form a saturated heterocyclic ring}, or taken together with P form a 4 to 7-membered heterocyclic ring;

R$_6$ is $C_1$–$C_7$ alkyl, halo$C_1$–$C_7$alkyl, carbo$C_1$–$C_7$alkoxy, —NR$_9$R$_{10}$ where R$_9$ and R$_{10}$, being the same or different, are $C_1$–$C_7$ alkyl or phenyl (optionally substituted with 1 or 2 groups selected from halo, lower alkyl, halo$C_1$–$C_7$alkyl, nitro, cyano, $C_1$–$C_7$ alkoxy);

R$_{24}$ is hydrogen, halogen or $C_1$–$C_7$ alkyl;

R$_{25}$ is hydrogen or halogen;

R$_{14a}$ and R$_{14b}$, being the same or different, are selected from hydrogen, hydroxy, $C_1$–$C_6$ alkyl, $C_1$–$C_6$ alkoxy, $C_1$–$C_6$ alkenyl, $C_1$–$C_6$ alkenyl-$C_1$–$C_6$ alkoxy, $C_1$–$C_6$ alkynyl-$C_1$–$C_6$ alkoxy, $C_1$–$C_6$ alkynoyloxy, poly $C_1$–$C_6$ alkoxy-$C_1$–$C_6$ alkoxy, phenyl, phenyl-$C_1$–$C_6$ alkyl, tri-$C_1$–$C_6$ alkylsilyloxy, diphenylphosphoryloxy and halogen, or R$_{14a}$ and R$_{14b}$ together form the epoxide or =CH$_2$;

R$_{18a}$ is hydrogen, $C_1$–$C_7$ alkyl, $C_2$–$C_8$ alkoxyalkyl, $C_2$–$C_8$ alkenyl, $C_2$–$C_8$ alkynyl or benzyl; the broken line between carbons 24 and 25 represents a single or double bond.

The carbon content of various hydrocarbon containing moieties is indicated by a prefix designating the minimum and maximum number of carbon atoms in the moiety, i.e., the prefix $C_i$–$C_j$ indicates a carbon atoms content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the above, "$C_1$–$C_7$ alkyl" is intended to include those alkyl groups of from 1 to 7 carbon atoms in either a straight or branched represents a double bond between chain. Examples of such lower alkyl groups are methyl, ethyl, propyl, isopropyl, butyl, sec-butyl, tert-butyl, pentyl, hexyl, heptyl and the like.

Cyclo($C_3$–$C_8$)alkyl is intended to include alkyl rings of 3 to 8 members. Examples of cyclo($C_3$–$C_8$)alkyl groups are cyclopropyl, cyclobutyl, cyclopentyl, cyclohexyl, cycloheptyl, bicyclo[2.2.1]heptyl, and the like.

$C_1$–$C_8$ alkoxy is intended to include those alkoxy groups of from 1 to 8 carbon atoms in either a straight or branched chain. Examples of such $C_1$–$C_8$ alkoxy groups are methoxy, ethoxy, propoxy, isopropoxy, butoxy, sec-butoxy, pentoxy, hexoxy, heptoxy, and the like.

$C_2$–$C_7$alkanoyl is intended to include those alkanoyl groups of from 2 to 7 carbon atoms in either a straight or branched chain. Examples of such $C_2$–$C_7$alkanoyl groups include acetyl, propionyl, isopropionyl, butyryl, pentanoyl, hexanoyl and the like.

$C_{10}$–$C_{24}$alkanoyl (—C(O)$C_9$–$C_{23}$alkyl) is intended to include those alkanoyl groups of from 10 to 24 carbon atoms in either a straight or branched chain. Examples of such $C_{10}$–$C_{24}$alkanoyl groups include decanoyl [—C(O)(CH$_2$)$_9$CH$_3$], lauroyl [—C(O)(CH$_2$)$_{10}$CH$_3$], tridecanoyl [—C(O)(CH$_2$)$_{11}$CH$_3$], myristoyl [—C(O)(CH$_2$)$_{12}$CH$_3$], pentadecanoyl [—C(O)(CH$_2$)$_{13}$CH$_3$], palmitoyl [—C(O)(CH$_2$)$_{14}$CH$_3$], magaroyl [—C(O)(CH$_2$)$_{15}$CH$_3$], stearoyl [—C(O)(CH$_2$)$_{16}$CH$_3$], arachidoyl [—C(O)(CH$_2$)$_{18}$CH$_3$], heneicosanoyl [—C(O)(CH$_2$)$_{19}$CH$_3$], behenoyl [—C(O)(CH$_2$)$_{20}$CH$_3$], tricosanoyl [—C(O)(CH$_2$)$_{21}$.CH$_3$], tetracosanoyl [—C(O)(CH$_2$)$_{22}$CH$_3$], and the like.

$C_{10}$–$C_{24}$alkenoyl (—C(O)$C_9$–$C_{23}$alkenyl) is intended to include those unsaturated groups of from 10 to 24 carbon atoms in either a straight or branched chain. Examples of such $C_{10}$–$C_{24}$ alkenoyl groups include undecylenoyl [—C(O)(CH$_2$)$_7$CH:CHCH$_3$], oleoyl [—C(O)(CH$_2$)$_7$CH:CH(CH$_2$)$_7$CH$_3$], linoloyl [—C(O)(CH$_2$)$_7$CH:CH.CH$_2$.CH:CH(CH$_2$)CH$_3$], and the like.

The term "$C_2$- alkoxyalkyl" is intended to include those lower alkoxy substituted lower alkyl groups containing from 2 to 8 carbon atoms and from 1 to 3 oxygen atoms in either a straight or branched chain. Examples of such $C_2$–$C_8$ alkoxyalkyl groups include methoxymethyl, methoxyethoxymethyl, methoxyethoxyethoxymethyl, ethoxyethyl, and the like. Examples of $C_1$–$C_8$ alkoxymethyl are methoxymethyl, ethoxymethyl, propoxymethyl, butoxymethyl, pentoxymethyl, butoxymethyl, pentoxymethyl, hexoxymethyl, and heptoxymethyl, and isomeric forms thereof.

The term alkanoyloxymethylene is intended to include those alkanoyloxy substituted methylenes containing from 2 to 8 carbon atoms in either a straight or branched chain. Examples of such $C_2$–$C_8$ alkanoyloxymethylene groups include acetoxymethyl, tert-butoxymethyl, n-propoxymethyl, valeroxymethyl and the like.

The term "substituted benzoyloxymethylene" is intended to include those benzoyloxymethyl groups in which the benzene ring is substituted with from 0 to 3 substituents selected from lower alkyl, trifluoromethyl, $C_1$–$C_7$ alkoxy, nitro, or cyano groups, and halogen atoms.

The term "substituted benzenesulfonyl" is intended to include those benzenesulfonyl groups in which the benzene ring is substituted with from 0 to 3 substituents selected from lower alkyl, trifluoromethyl, $C_1$–$C_7$ alkoxy, nitro, or cyano groups, and halogen atoms.

The term "halogen" is intended to include the halogen atoms fluorine, chlorine, bromine and iodine.

The term "halo $C_1$–$C_7$alkyl" is intended to include those halogen substituted $C_1$–$C_7$ alkyl groups containing from 1 to 7 carbon atoms in either a straight or branched chain and from 1 to 3 halogen atoms. Examples of halo$C_1$–$C_7$alkyl include fluoromethyl, 2-bromoethyl, 3-chloropropyl, 5-iodopentyl, trifluoromethyl, and the like.

The term "$C_2$–$C_8$ alkenyl" is intended to include those lower alkyl groups containing from 2 to 8 carbon atoms in either a straight or branched chain which contains 1 to 2 carbon double bonds. Examples of such $C_2$–$C_8$ alkenyl groups include allyl, 3-butenyl, 2,4-pentadienyl, hexenyl, and the like.

The term "$C_2$–$C_8$ alkynyl" is intended to include those alkynyl groups containing from 1 to 8 carbon atoms in either a straight or branched chain which contains 1 to 2 carbon-carbon triple bonds. Examples of such $C_2$–$C_8$ alkynyl groups include propargyl, 2-butynyl, 2,4-pentadiynyl, 5-hexynyl, and the like.

Examples of "alkoxycarbonyl" (—C(=O)O—(CH$_2$)$_p$— $C_1$–$C_7$ alkoxy) include ethoxycarbonyl, isopropoxycarbonyl, methoxycarbonyl, butoxycarbonyl, hexoxycarbonyl and the like.

$C_1$–$C_7$ alkanoyl is intended to include alkyl groups of from 1 to 7 carbon atoms in either a straight or branched chain. Examples of $C_1$–$C_7$ alkanoyl include acetyl, propionyl, iso-butyryl, valeryl, 5-methylhexanoyl, and the like.

Examples of aminocarbonyl (—C(=O)NR$_4$R$_5$) include dimethylaminocarbonyl, propylmethylaminocarbonyl, dibutylaminocarbonyl, isopropylaminocarbonyl, hexylaminocarbonyl and the like.

Examples of aminothiocarbonyl (—C(=S)NR$_4$R$_5$) include dimethylaminothiocarbonyl, propylmethylaminothiocarbonyl, dibutylaminothiocarbonyl, isopentylaminothiocarbonyl, hexylaminothiocarbonyl and the like.

Examples of the group —P(=X)(R$_2$)(R$_3$) include diethyl thiophosphoryl, phenylmethoxyphosphonyl, 2-thioxo-1,3,2-dioxaphosphorinanyl, N,N-dimethylmethoxyphosphoramidyl, diphenylphosphinyl and the like.

Examples of —SR$_6$ include 2,4-dinitrobenzenesulfenyl, dimethylaminosulfenyl, ethoxycarbonylsulfenyl, trichloromethylsulfenyl, 4-morpholinosulfenyl and the like.

Examples of —SO$_2$NR$_4$R$_5$ include dimethylsulfamoyl, phenylmethylsulfamoyl, 4-morpholinosulfamoyl, piperidinylsulfamoyl and the like.

The term "P containing heterocyclic ring" is intended to include 1,3-dioxa-2-phosphorinane, 1-aza-3-oxa-2-phospholane, 1,3-diaza-2-phospholane, 1-thia-3-oxa-2-phospholane, and the like.

Examples of heterocyclic amine rings according to —NR$_4$R$_5$, —NR'$_4$R'$_5$ and —NR$_7$R$_8$ are:
4-morpholine,
4phenyl-1-piperazine,
4-(2-pyridinyl)-1-piperazine,
2,6-dimethyl-4-morpholine,
1-pyrroldine,
4-methyl-1-piperazine,
1-piperidine,
4-phenyl-1-piperidine thiazolidine,
4-phenyl-1,2,3,6-tetrahydropyridine,
4-phenylpiperidine,
ethyl prolinate,
tetrahydrofurylamine,
3-pyrrolne,
thiazolidine-4carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine,
N-carboethoxypiperazine, Pharmaceutically acceptable salts means salts useful for administering the compounds of this invention and include mesylate, hydrochloride, hydrobromide, hydroiodide, sulfate, phosphate, acetate, propionate, lactate, maleate, malate, succinate, tarrrate, and the like. These salts may be in hydrated form.

Preferred compounds of this invention are compounds of Formula I (as well as Formula II, III, IV and V) where R$_{24}$ and R$_{25}$ are hydrogen; R$_{18a}$ is hydrogen, $C_1$–$C_4$ alkyl, $C_2$–$C_4$ alkoxyalkyl, $C_2$–$C_4$ alkenyl or benzyl; and the broken line between carbons 24 and 25 represents a double bond.

Examples of the compounds of Formula II of this invention are as follows:
18-thiomarcfortine A
1-acetoxymethyl-18-thiomarcfortine A
1-diethoxyphosphoryl-18-thiomarcfortine A
1-dimethylsulfamoyl-18-thiomarcfortine A
1-cyclopropylcarbonyl-18-thiomarcfortine A
2-bicyclo[2.2.1]heptanoyl-18-thiomarcfortine A
1-(1-piperidinyl)thiocarbonyl-18-thiomarcfortine A
1-succinoyl-18-thiomarcfortine A
1-(4-morpholinosulfenyl)-18-thiomarcfortine A
1-(2,4-dinitrobenzenesulfenyl)-18-thiomarcfortine A
24-propoxy-24,25-dihydro-18-thiomarcfortine A
1-(p-toluenesulfonyl)-18-thiomarcfortine A
1-acetyl-18-thiomarcfortine A
1-methyl-18-thiomarcfortine A
1-benzyl-18-thiomarcfortine A
1-methylcarbamoyl-18-thiomarcfortine A
1-methoxycarbonyl-18-thiomarcfortine A
24,25-dihydro-18-thiomarcfortine B
24-methoxy-24,25-dihydro-18-thiomarcfortine B
1-(p-toluenesulfonyl)-18-thiomarcfortine B
1-ethyl-18-thiomarcfortine B
1-benzyl-18-thiomarcfortine B
18a-ethyl-18-thiomarcfortine B
18a-benzyl-18-thiomarcfortine B
18a-methoxyethoxymethyl-18-thiomarcfortine B
18a-allyl-18-thiomarcfortine B
18a-propargyl-18-thiomarcfortine B
18a-ethyl-24-methoxy-24,25-dihydro-18-thiomarcfortine B
1,18a-bis-ethyl-18-thiomarcfortine B
1,18a-bis-benzyl-18-thiomarcfortine B
18a-ethyl-24-methoxy-18-thiomarcfortine B
1-(2,4-dinitrobenzene sulfonyl)-18a-ethyl-24-methoxy-24,25-dihydro-18-thiomarcfortine B
18a-ethyl-24,25 dihydro-18-thiomarcfortine B
24,25 dihydro-18-thiomarcfortine C
1-(p-bromobenzene sulfonyl)-18-thiomarcfortine C
1-propionyl-18-thiomarcfortine C
1-propyl-18-thiomarcfortine C
1-benzyl-18-thiomarcfortine C
18a-propyl-18-thiomarcfortine C
18a-benzyl-18-thiomarcfortine C
18a-methoxyethoxymethyl-18-thiomarcfortine C
18-allyl-18-thiomarcfortine C
18a-propargyl-18-thiomarcfortine C
1,18a-bis-propyl-18-thiomarcfortine C
1,18a-bis-benzyl-18-thiomarcfortine C
18-thiomarcfortine C
1-(4-carbethoxy-1,3-thiazolidinin-3-yl)carbonyl-18-thiomarcfortine A
1-palmitoyl-18-thiomarcfortine A
1-(4-morpholinocarbonyl)-18-thiomarcfortine A.

Examples of the compounds of Formula m of this invention are as follows:
18-thioparaherquamide 24,25-dihydro-18-thioparaherquamide
14-O-methyl-18-thioparaherquamide
14-O-ethyl-18-thioparaherquamide
14-O-butyl-18-thioparaherquamide
14O-benzyl-18-thioparaherquamide
14-O-ally-18-thioparaherquamide
14-O-propargyl-18-thioparaherquamide
14-O-methoxymethyl-18-thioparaherquamide
14-O-methoxy-ethoxy-18-thioparaherquamide
14-O-methoxy-ethyoxy-methyl-18-thioparaherquamide
17-methyl-18-thioparaherquamide
17-methylene-18-thioparaherquamide
1-N-(p-toluenesulfonyl)-18-thioparaherquamide
24-methoxy-24,25-dihydro-18-thioparaherquamide Examples of the compounds of Formula IV of this invention are as follows:

1-diethoxythiophosphoryl-marcfortine A
1-phenylmethoxyphosphonyl-marcfortine A
1-cycdohexylcarbonyl-marcfortine A
1-(1-piperidinyl)thiocarbonyl-marcfortine A
1-N-(4-carbethoxy-1,3-thiazolidinin-3-yl)carbonyl-marcfortine A
1-succinoyl-marcfortine A
1-(4-oxopentanoyl)-marcfortine A
1-dimethylaminoacetyl-marcfortine A
1-N,N-dimethylsuccinamidoyl-marcfortine A
1-cyclopropylcarbonyl-18a-ethyl-marcfortine B
1-dimethylaminosulfenyl-18a-N-benzyl-marcfortine B
1-ethoxycarbonylsulfenyl-18a-N-methoxyethoxymethyl-marcfortine B
1-diphenylphosphinyl-18a-N-allyl-marcfortine B
1-(3-acetoxy)propionyl-18a-N-propargyl-marcfortine B
1-(2,4dichlorophenoxy)carbonyl-18a-N-ethyl-24-methoxy-24,25-dihydro-marcfortine B
1-N-(2,4dinitrobenzenesulfenyl)-18a-N-ethyl-marcfortine B
1-N-(p-bromobenzenesulfenyl)-marcfortine C
1-acetozymethyl marcfortine C
1-diethoxythuophosphoryl-marcfortine C
1-phenylmethoxyphosphonyl-marcfortine C
1-cyclopropylcarbonyl-marcfortine C
1-cyclohexylcarbonyl-marfortine C
1-(1-piperidinyl)thiocarbonyl-marcfortine C
1-N-(4-carbethoxy-1,3-thiazolidinin-3-yl)carbonyl-marcfortine C
1-succinoyl-marcfortine C
1-(4-morpholinosulfenyl)-marcfortine C
1-phenoxycarbonyl-marcfortine C
1-(4-oxopentanoyl)-marcfortine C
1-dimethylaminoacetyl-marcfortine C
1-N,N-dimethylsuccinamidoyl-marcfortine C
1-palmitoyl-marcfortine A; preferably
1-cyclopropylcarbonyl-marcfortine A
1-phenoxycarbonyl-marcfortine A
1-palmitoyl-marcfortine A
1-[[(4-nitrophenyl)oxy]carbonyl]-marcfortine A
1-(1-piperidinecarbonyl)-marcfortine A
1-[[4-(ethoxycarbonyl)piperazin-1-yl]carbonyl]-marcfortine A
1-[[4-(benzyl)piperazin-1-yl]carbonyl]-marcfortine A
1-[[4-(1,3-benzodioxol-5-yl-methyl)piperazin-1-yl]carbonyl]-marcfortine A
1-[[4-(methyl)piperazin-1-yl]carbonyl]-marcfortine A
1-(1,3-dihydro-1,3-dioxo-2H-isoindol-2-yl)-marcfortine A
1-[[4-(pyridin-2-yl)piperazin-1-yl]carbonyl]-marcfortine A
1-[[4-(phenyl)piperazin-1-yl]carbonyl]-marcfortine A
1-[[4-(chlorocarbonyl)piperazin-1-yl]carbonyl]-marcfortine A
1-[[4-(phenyl)piperidin-1-yl]carbonyl]-marcfortine A
1-[[4-(dimethyl)piperidin-1-yl]carbonyl]-marcfortine A
1-[[4-(5-chloropyridazin-3-yl)piperazin-1-yl]carbonyl]-marcfortine A
1-[[4-(4chlorophenyl)piperazin-1-yl]carbonyl]-marcfortine A
1-[[4-(trichloroethoxycarbonyl)piperazin-1-yl]carbonyl]-marcfortine A
1-[[4-(3-trifluoromethyl-thiadiazol-1-yl)piperazin-1-yl]carbonyl]-marcfortine A
1-acetoxymethyl-marcfortine A
1-(2,4dinitrobenzenesulfenyl)-marcfortine A
1-(4-morpholinosulfenyl)-marcfortine A
1-(trichloromethylsulfenyl)-marcfortine A
1-(methoxycarbonylsulfenyl)-marcfortine A
1-(benzeresulfenyl)-marcfortine A
1-(2-tetrahydrofuranyl)-marcfortine A, and
more preferably,
1-(4morpholinocarbonyl)-marcfortine A or
1-(4morpholinocarbonyl)-marcfortine A N-oxide.

Examples of the compounds of Formula V of this invention are as follows:

1-acetoxymethyl-paraherquamide
1-diethoxythiophosphoryl-paraherquamide
1-phenylmethoxyphosphonyl-paraherquamide
1-cyclopropylcarbonyl-paraherquamide
1-cyclohexylcarbonyl-paraherquamide
1-(1-piperidinyl)thiocarbonyl-paraherquamide
1-N-(4-carbethoxy-1,3-thiazolidinin-3-yl)carbonyl-paraherquamide
1-succinoyl-paraherquamide
1-(4-morpholinosulfenyl)-paraherquamide
1-phenoxycarbonyl-paraherquamide
1-(4-oxopentanoyl)-paraherquamide
1-dimethylaaminoacetyl-paraherquamide
1-N,N-dimethylsuccinamiidoyl-paraherquamide
1-palmitoyl-paraherquamide
1-(4-morpholinocarbonyl)-paraherquamide.

The compounds of Formula II are prepared by the following procedures: It has been found, unexpectedly, that treatment of the Marcfortines A, B, and C, or suitably substituted C-24, C-25, N-1 and N-18a derivatives thereof, with phosphorous pentasulfide or, preferably, 2,4bis (methoxyphenyl)-1,3-dithia-2,4diphosphetane-2,4-disulfide (Lawesson's reagent) selectively provides the corresponding 18-thio- derivatives. Suitable C-24, C-25, N-1 and N-18a substituted marcfortine A, B and C derivatives for this reaction are readily prepared by the procedures given in U.S. Pat. No. 4,923,867, the disclosure of which is incorporated herein by reference. The reactions are conducted in a suitable inert solvent such as pyridine, collidine, toluene (preferred), xylene, dioxane, tetrahydrofuran, and the like, at temperatures from 10° to 180° preferably 80° to 140°.

Alternatively, the C-24, C-25 and N-1 derivatives can be prepared from the 18-thiomarcfortine. For example, a large series of 18-thiomarcfortine analogs can be prepared by alkylation or acylation of N-1 of the N-18a substituted 18-thiomarcfortine. These derivatives may be easily prepared by sequential treatment of a solution of 18-thiomarcfortine A, N-18a-substituted 18-thiomarcfortine B, or N-18a-substituted 18-thiomarcfortine C in an aprotic organic solvent such as tetrahydrofuran, ether, benzene and the like with an excess of a strong base such as potassium hydride (preferred), sodium hydride, butyllithium, potassium tert-butoxide, and the like followed by a suitable alkylating or acylating agent at temperatures ranging from 0° C. to 50° C. for 0.25 to 48 hours. Suitable alkylating agents include alkyl bromides, alkyl iodides, alkyl sulfonates, alkenyl iodides, alkynyl bromides, alkoxyalkyl chlorides, and the like. Suitable acylating agents include acyl anhydrides, acyl chlorides, acyl bromides, substituted benzenesulfonyl chlorides, substituted benzenesulfonic anhydrides, sulfenyl chlorides, isocyanates, carbamoyl chlorides, chloroformates, and the like.

An additional series of derivatives can be generated by modification of the C24-C25 double bond of 18-thiomarcfortine A, B and C. The 24,25 dihydro analogs are readily prepared by stirring a solution of the appropriate 18-thiomarcfortine in an alcoholic solvent such as methanol, ethanol, propanol and the like with a catalyst such as palladium, platinum, tris (triphenylphosphine)-chlororhodium and the like in the presence of hydrogen gas. The product, which is a 24,25-dihydro-18-thiomarcfortine analog, can be isolated and purified by using techniques known to those skilled in the art. Note that the reactions described above for modification of other portions of the 18-thiomarcfortine structure may also be applied to 24,25-dihydro 18-thiomarcfortine analogs to prepare the corresponding 24,25-dihydro analogs. Additional $C_{24}$-$C_{25}$ double bond modified analogs of the 18-thiomarcfortine may be prepared via the 24,25 dibromide which is easily prepared by treating a solution of a 18-thiomarcfortine in a halogenated solvent such as dichloromethane, chloroform, carbon tetrachloride and the like with 1 molar equivalent of bromine at temperatures ranging from −20° C. to 25° C. for 0.25 to 8 hours. This process affords the corresponding 24,25-dibromo 24,25-dihydro-18-thiomarcfortine derivative which can be isolated and purified by using techniques known to those skilled in the art. Note that the 24,25 dichloro analog may be prepared by substituting chlorine for bromine in the process described above. The 24,25-dibromo 24,25-dihydro-18-thiomarcfortine analogs described above are useful intermediates for the preparation of additional derivatives. Thus, treatment of a solution of the dibromide in an alcoholic solvent such as methanol, ethanol, propanol, and the like with a strong base such as 1,8-diazabicyclo [5.4.0]undec-7-ene (DBU) at temperatures ranging from 0° C. to 30° C. for 0.25 to 24 hours affords 24-alkoxy-25-bromo-24,25 dihydro-18-thiomarcfortine analogs which can be isolated and purified by using techniques known to those skilled in the art. These 24 alkoxy, 25-bromo derivatives can be debrominated by treatment of a solution of the compound in an aprotic organic solvent such as benzene, toluene, hexane, and the like with a tin hydride reducing agent such as tri-butyl tin hydride, tri-phenyl tin hydride and the like with or without the addition of a radical initiator such as azobis-isobutyronitrile (AIBN) at temperatures ranging from 25° C. to 120° C. for 0.5 to 48 hours. This process affords the corresponding 24-alkoxy-18-thiomarcfortine derivatives ($R_{24}$=lower alkoxy in the general structure) which can be isolated and purified by using techniques known to those skilled in the art.

General procedures for the preparation of heteroaromatic N-oxides can be found in Chapter II of "Chemistry of the Heterocyclic N-Oxides", A. R. Katritzky and J. M. Lagowski, published 1971 Academic Press (Vol. 19 of ORGANIC CHEMISTRY—A Series of Monographs). Typically the N-oxide is formed by reaction with a percarboxylic acid in an appropriate solvent. Most suitably an aromatic peracid in a non-polar solvent is used, since the reaction may usually be carried out at room temperature. Suitable aromatic peracids include perbenzoic acid, chloroperbenzoic acid and perphthalic acid.

The compounds of Formula III are prepared by the following procedures: Treatment of paraherquamide and derivatives thereof, with phosphorous pentasulfide or, preferably, 2,4-bis(methoxyphenyl)-1,3-dithia-2,4-diphosphetane-2,4-disulfide (Lawesson's reagent) selectively provides the corresponding 18-thio- derivatives. Suitable paraherquamide derivatives for this reaction are readily prepared by the procedures given in U.S. Pat. Nos. 4,978, 656 and 4,873,247 as well as WO 91/09961, the disclosures of which are incorporated herein by reference. The reactions are conducted in a suitable inert solvent such as pyridine, collidine, toluene (preferred), xylene, dioxane, tetrahydrofuran, and the like, at temperatures from 10° to 180° preferably 80° to 140°.

Alteratively, the C-24, C-25 and N-1 derivatives can be prepared from the 18-thioparaherquamide. For example, a large series of 18-thioparaherquamide analogs can be prepared by alkylation or acylation of N-1 of the N-18a substituted 18-thioparaherquamide. These derivatives may be easily prepared by sequential treatment of a solution of 18-thioparaherquamide in an aprotic organic solvent such as tetrahydrofuran, ether, benzene and the like with an excess of a strong base such as potassium hydride (preferred), sodium hydride, butyllithium, potassium tert-butoxide, and the like followed by a suitable alkylating or acylating agent at temperatures ranging from 0° C. to 50° C. for 0.25 to 48 hours. Suitable alkylating agents include alkyl bromides, alkyl iodides, alkyl sulfonates, alkenyl iodides, alkynyl bromides, alkoxyalkyl chlorides, and the like. Suitable acylating agents include acyl anhydrides, acyl chlorides, acyl bromides, substituted benzenesulfonyl chlorides, substituted benzenesulfonic anhydrides, sulfenyl chlorides, isocyanates, carbamoyl chlorides, chloroformates, and the like.

An additional series of derivatives can be generated by modification of the $C_{24}$-$C_{25}$ double bond of 18-thioparaherquamides. The 24,25 dihydro analogs are readily prepared by stirring a solution of the appropriate 18-thioparaherquamide in an alcoholic solvent such as methanol, ethanol, propanol and the like with a catalyst such as palladium, platinum, tris (triphenylphosphine)-chlororhodium and the like in the presence of hydrogen gas. The product, which is a 24,25-dihydro-18-thioparaherquamide analog, can be isolated and purified by using techniques known to those skilled in the art. Note that the reactions described above for modification of other portions of the 18-thioparaherquamide structure may also be applied to 24,25-dihydro 18-thioparaherquamide analogs to prepare the corresponding 24,25-dihydro analogs. Additional $C_{24}$-$C_{25}$ double bond modified analogs of the 18-thioparaherquamides may be prepared via the 24,25 dibromide which is easily prepared by treating a solution of a 18-thioparaherquamide in a halogenated solvent such as dichloromethane, chloroform, carbon tetrachloride and the like with 1 molar equivalent of bromine at temperatures ranging from −20° C. to 25° C. for 0.25 to 8 hours. This process affords the corresponding 24,25-dibromo 24,25-dihydro-18-thioparaherquamide derivative which can be isolated and purified by using techniques known to those skilled in the art. Note that the 24,25 dichloro analog may be prepared by substituting chlorine for bromine in the process described above. The 24,25-dibromo 24,25-dihydro-18-thioparaherquamide analogs described above are useful intermediates for the preparation of additional derivatives. Thus, treatment of a solution of the dibromide in an alcoholic solvent such as methanol, ethanol, propanol, and the like with a strong base such as 1,8-diazabicyclo[5.4.0] undec-7-ene (DBU) at temperatures ranging from 0° C. to 30° C. for 0.25 to 24 hours affords 24-alkoxy-25 bromo-24, 25 dihydro-18-thioparaherquamide analogs which can be isolated and purified by using techniques known to those skilled in the art. These 24 alkoxy, 25-bromo derivatives can be debrominated by treatment of a solution of the compound in an aprotic organic solvent such as benzene, toluene, hexane, and the like with a tin hydride reducing agent such as tri-butyl tin hydride, tri-phenyl tin hydride and the like with or without the addition of a radical initiator such as azobis-isobutyronitrile (AIBN) at temperatures ranging from 25° C. to 120° C. for 0.5 to 48 hours. This process affords the corresponding 24-alkoxy-18-thioparaherquamide derivatives ($R_{24}$=lower alkoxy in the general structure) which can be isolated and purified by using techniques known to those skilled in the art.

General procedures for the preparation of heteroaromatic N-oxides can be found in Chapter II of "Chemistry of the Heterocyclic N-Oxides", A. R. Katritzky and J. M. Lagowski, published 1971 Academic Press (Vol. 19 of ORGANIC CHEMISTRY—A Series of Monographs). Typically the N-oxide is formed by reaction with a percarboxylic acid in an appropriate solvent. Most suitably an aromatic peracid in a non-polar solvent is used, since the reaction may usually be carried out at room temperature. Suitable aromatic peracids include perbenzoic acid, chloroperbenzoic acid and perphthalic acid.

The compounds of Formula IV are prepared by alkylation or acylation of N-1 of marcfortine A and N-18a substituted marcfortines B and C. These derivatives may be easily prepared by sequential treatment of a solution of marcfortine A, or N-18a substituted marcfortines B or C in an aprotic organic solvent such as tetrahydrofuran, ether, benzene and the like with an excess of a strong base such as potassium hydride (preferred), sodium hydride butyllithium, potassium tert-butoxide, and the like followed by a suitable alkylating or acylating agent at temperatures ranging from 0° C. to 50° C. for 0.25 to 48 hours. Suitable alkylating or acylating agents include alkanoyloxyalkyl bromides, aminosulfenyl chlorides, phosphoryl chlorides, phosphonyl chlorides, acyl anhydrides, acyl chlorides, acyl bromides, substituted benzenesulfenyl chlorides, carbamoyl chlorides, substituted phenoxychloroformates, and the like. Treatment of marcfortine A and N-18a substituted marcfortines B and C and $C_{24}C_{25}$ modified marcfortines under these conditions affords 1-N-substituted analogs which can be isolated and purified by using techniques known to those skilled in the art The compounds of Formula V are prepared by alkylation or acylation of N-1 of paraherquamide. These derivatives may be easily prepared by sequential treatment of a solution of paraherquamide in an aprotic organic solvent such as tetrahydrofuran, ether, benzene and the like with an excess of a strong base such as potassium hydride (preferred), sodium hydride butyllithium, potassium tert-butoxide, and the like followed by a suitable alkylating or acylating agent at temperatures ranging from 0° C. to 50° C. for 0.25 to 48 hours. Suitable alkylating or acylating agents include alkanoyloxyalkyl bromides, aminosulfenyl chlorides, phosphoryl chlorides, phosphonyl chlorides, acyl anhydrides, acyl chlorides, acyl bromides, substituted benzenesulfenyl chlorides, carbamoyl chlorides, substituted phenoxychloroformates, and the like. Treatment of paraherquamide under these conditions affords 1-N-substituted analogs which can be isolated and purified by using techniques known to those skilled in the art.

General procedures for the preparation of heteroaromatic N-oxides can be found in Chapter II of "Chemistry of the Heterocyclic N-Oxides", A. R. Katritzky and J. M. Lagowski, published 1971 Academic Press (Vol. 19 of ORGANIC CHEMISTRY—A Series of Monographs). Typically the N-oxide is formed by reaction with a percarboxylic acid in an appropriate solvent. Most suitably an aromatic peracid in a non-polar solvent is used, since the reaction may usually be carried out at room temperature. Suitable aromatic peracids include perbenzoic acid, chloroperbenzoic acid and perphthalic acid.

PREPARATION OF STARTING MATERIAL

Paraherquamide is isolated from Penicillium Sp. IMI 332995 and/or *Penicillium charlessi* MF 5123 (ATCC 20841) using standard fermentation and isolation techniques. The isolation is described in detail in U.S. Pat. Nos. 4,873,247 and 4,978,656 as well as EP 390532-A, EP-301742-A and WO 91/09961 (all of which are incorporated herein by reference).

PREPARATION OF STARTING MATERIAL

N-18a substituted marcfortines B and C and C24-C25 modified marcfortines are readily prepared by procedures given in U.S. Pat. No. 4,923,867, the disclosure of which is incorporated herein by reference.

Marcfortines A, B and C are isolated, along with the previously known roquefortine, as fungal metabolites of *Penicillium roqueforti* using standard fermentation and isolation techniques. The isolation, as well as the analytical and structural characteristics of marcfortine A, are described in detail in Polonsky et al *Journal of the Chemical Society Chemical Communications* 1980, 601–602. The isolation, as well as the analytical and structural characteristics of marcfortines B and C, are described in detail in Polonsky et al *Tetrahedron Letters* 1981, 22, 1977–1980.

Alternatively, and more preferably, Marcfortines A and C may be isolated from Penicillium sp. UC7780 (strain number in Upjohn Culture Collection, UC 7780, The Upjohn Company, Kalamazoo, Mich.). This strain was isolated from a soil sample collected in Illinois, deposited in the U.S. Department of Agriculture patent culture collection in Peoria, Ill. and given the accession number NRRL 18887. To further characterize the fungus a taxonomy study was done following the methods and materials described by I. John Pitt, The Genus *Penicillium*, Academic Press, London, (1979). Spore and hyphae surfaces were examined by scanning electron microscopy according to the methods of Dietz, A. and Matthews, J, Appl. Microbiology 18: 694–696 (1969). Intact conidiophores are visualized by light microscopy [A.H.S. Onions et al., Smith's Introduction to Industrial Mycology, John Wiley and Sons, New York, pp 301–302 (1979)] after slide culture(s) are prepared: A glass petri dish containing glass beads, microscope slide, and coverslip are sterilized. A small block of potato dextrose agar is placed on the slide and inoculated on four sides with the fungus culture. The coverslip is set on the inoculated agar block and sterile water added to maintain moisture. The chamber is incubated for six days at 24° C. A slide is prepared by removing the coverslip and placing it on a drop of lactophenol cotton blue stain.

The characteristics of Penicillium sp. UC 7780 (NRRL 18887) are as follows:

Morphology—a biverticillate penicillus (two branch points between conidium and stipe). These branches (metulae) support the phialides or conidia bearing structures. Conidiophores (approximately 35 μm) terminated in verticils of 2–5 (10–14 μm) metulae. Phialides were ampulliform (like an ancient Greek wine jar) in verticils of 2–5 (7 μm). Conidia were smooth and spheroidal (2 μm) typically appearing in long columns. The stipe walls were smooth.

The culture was inoculated onto three petri dishes of Czapek yeast agar (CYA), one being 6 cm in diameter and one each of malt extract agar (MEA) and 25% glycerol nitrate agar (G25N). Inoculation was made from a semisolid suspension (0.5 ml of 0.2% agar with 0.05% Tween 80). An inoculating loop of conidia was added to the tube and mixed. A loop of suspension was inoculated in a pattern of three sites per plate. A needle was used to stab inoculate the 6 cm plate. The incubation regime was: one CYA plate plus the MEA and G25N plates at 24° C., one CYA plate at 37° C., and the 6 cm CYA plate at 5° C. After seven days the colony diameters, colors, and other characters were recorded and are set forth in Table I. On potato dextrose agar (PDA, Difco) agar, a deep red color on the bottom or reverse of the colony is produced.

No sexual stage was noted. This results in the culture (NRRL 18887) being keyed in the Penicillium Key to subgenera. Within the Penicilliun Key, the penicillus type alone determines the subgenus to which a species is allocated. This species has several characteristics that distinguish it from the Biverticillium subgenus even though its penicillus is biverticilliate. The species consistently produces colonies greater than 10 mm in diameter in 7 days on glycerol nitrate agar. The metulae appear longer than the phialides and are in verticils of 2–5. These characteristics place this Penicillium sp. (NRRL 18887) into the subgenus Furcatum.

The foregoing description is illustrative of a strain of Penicillium sp. UC 7780 (NRRL 18887) which can be employed in the production of Marcfortine and derivatives thereof. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

This description is also desired and intended to include inter- and intraspecific genetic recombinants produced by genetic techniques well known to those skilled in the art, such as, for example, conjugation, transultion and genetic engineering techniques.

Penicillium sp. UC 7780 (NRRL 18887) may be cultivated under aerobic condition in the same manner as commonly employed in the art for cultivation of a known strain of the genus Penicillium.

As medium components may be employed any of the well-known nutrient materials for Penicillium. For instance, as an assimilable carbon source, glucose, glycerol, maltose, dextrin, starch, lactose, sucrose, molasses, soybean oil, cotton seed oil, etc., preferably glucose and glycerol may be employed and, as an assimilable nitrogen source, soybean meal, peanut meal, cotton seed meal, fish meal, corn steep liquor, peptone, rice, bran, meat extract, yeast, yeast extract, sodium nitrate, ammonium nitrate, ammonium sulfate, etc. may be used. And, such inorganic salts as sodium chloride, phosphates, calcium carbonate, etc. may be added to a culture medium. A minor amount of a metal salt may also be added, if necessary. Further, a minor amount of a heavy metal may be added, if necessary.

Particularly, in cultivating the Penicillium sp. (NRRL 18887) under aerobic condition, ordinary aerobic cultivation methods such as, for example, solid culture, culture under aeration and agitation, shaken culture etc. may be favorably utilized. Trace metals, for example, zinc, magnesium, manganese, cobalt, iron and the like should be be added to the fermentation medium since reverse-osmosis grade water must be supplemented.

In carrying out cultivation with aeration and agitation, an anti-foaming agent, e.g., silicon oil, vegetable oils, surfactants, etc. may be suitably employed.

The pH of the medium may be usually within a pH range of 3–9 and preferably within or around neutral range and cultivation temperatures may be usually of 20°–30° C., in particular about 21° C. being preferred.

Cultivation may be continued until Marcfortine A will be substantially accumulated in a culture medium, usually for 20 hours to 240 hours, preferably for 48 hours to 168 hours and, after cultivation, Marcfortine A may be isolated and recovered from a cultured broth by a suitable combination of various method. For example, there may be extraction with an organic solvent, e.g. ether, ethyl acetate or chloroform; dissolution into a more polar solvent, e.g. acetone or alcohol; removal of impurities with a less polar solvent, e.g. petroleum ether or hexane, adsorptive chromatography with active carbon or silica gel; gel filtration through a column of "sephadex" (available from Pharmacia Co., Ltd, U.S.A.); and so on.

Marcfortine B can be prepared from Marcfortine A by biotransformation using a microorgainism in an aqueous nutrient medium containing an assimilable source of carbon and an assimilable source of nitrogen under aerobic conditions. The present invention also provides:

Biologically pure cultures of the (Organisms obtained from culture collection as obviously discovered entities) genus Cunninghamella, characterized as species selected from the group consisting of NRRL 1368, 1393 or 3655 and ATCC 8688a.

A method of using members of genus Cunninghamella, characterized as species selected from the group consisting of NRRL 1368, 1393 or 3655, and ATCC 8688a to produce Marcfortine B which comprises:

adding Marcfortine A to metabolizing cultures of the cited microorganisms.

By "biotransformation" is meant the use of microorganisms and/or isolated, partially purified enzymes for the converstion of a given substrate into a useful product. H. G. Davies, et al., "Biotransformations in Preparative Organic Chemistry", Academic Press, N.Y., 1989, p. IX.

By "metabolizing" is meant carrying out the processes of metabolism. A definition of metabolism may be found in A. L. Lehninger, "Principles of Biochemistry", Worth Publ., New York, 1982, p. 333.

By using the new method of the present invention, Marcfortine B is produced by adding Marcfortine A to growing cultures of cited microorganisms. The genus Cunninghamella is preferred for effecting this transformation, including *Cunninghamella echinulata* subsp. elegans (−) NRRL 1368, *Cunninghamella blakesleeana* (+) ATCC 8688a *Cunninghamelia echinulata* subsp. elegans NRRL 1393, *Cunninghamella echinulata* NRRL 3655; the strain NRRL 3655 is particularly preferred.

A subculture of *Cunninghamella echinulata* subsp. elegans (−) was deposited under the provisions of the Budapest Treaty in the permanent collection of the Northern Region Research Center, ARS; U.S. Dept. of Agriculture; Peoria, Ill., USA. Its accession number is NRRL 1368. A subculture of *Cunninghamella echinulata* subsp. elegans (−) was also deposited under the provisions of the Budapest Treaty in the permanent collection of the American Type Culture Collection, Rockville, Md., USA. Its accession number is ATCC 8688b.

A subculture of *Cunninghamella blakesleeana* (+) was deposited under the provisions of the Budapest Treaty in the permanent collection of the American Type Culture Collection, Rockville, Md., USA. Its accession number is ATCC 8688a A subculture of *Cunninghamella echinulata* subsp. elegans (−) was deposited under the provisions of the Budapest Treaty in the permanent collection of the Northern Region Research Center, ARS; U.S. Dept. of Agriculture; Peoria, Ill., USA. Its accession number is NRRL 1393. A subculture of *Cunninghamella echinulata* subsp. elegans (−) was also deposited under the provisions of the Budapest Treaty in the permanent collection of the American Type Culture Collection, Rockville, Md., USA. Its accession number is ATCC 10028b.

A subculture of *Cunninghamella echinulata* was deposited under the provisions of the Budapest Treaty in the permanent collection of the Northern Region Research Center, ARS; U.S. Dept of Agriculture; Peoria, Ill., USA. Its accession number is NRRL 3655.

The use of these microorganisms in the process of the present invention results in the production of Marcfortine B from Marcfortine A.

Marcfortine B is produced when *Cunninghamella echinulata* subsp. elegans (−) NRRL 1368, *Cunninghamella blakesleeana* (+) ATCC 8688a, *Cunninghamella echinulata* subsp. elegans (−) NRRL 1393 or *Cunninghamella echinulata* NRRL 3655 is fermented in an aqueous nutrient medium under submerged aerobic conditions in the presence of Marcfortine A. Typically the microorganism is fermented in a nutrient medium containing a carbon source and a proteinaceous material. Preferred carbon sources include glucose, brown sugar, sucrose, glycerol, starch, cornstarch, lactose, dextrin, molasses, and the like. Preferred nitrogen sources include cottonseed flour, corn steep liquor, yeast, autolyzed brewer's yeast with milk solids, soybean meal, cottonseed meal, cornmeal, milk solids, pancreatic digest of casein, distillers' solids, animal peptone liquors, meat and bone scraps, and the like. Combinations of these carbon and nitrogen sources can be used advantageously. Trace metals, for example, zinc, magnesium, manganese, cobalt, iron and the like need not be added to the fermentation medium since tap water and unpurified ingredients are used as medium components.

Production of Marcfortine B can be induced at any temperature conducive to satisfactory growth of the microorganism between about 23° and 32° C. and preferably at about 28° C. Ordinarily, optimum production of Marcfortine B is obtained in about 1 to 4 days after addition of Marcfortine A to the growing culture, and preferably in about 2 days. The fermentation broth normally remains weakly acid to basic (pH 5.8–9.0) during the fermentation. The final pH is dependent, in part, on the buffers present, if any, and in part on the initial pH of the culture medium. It is advantageously adjusted to about pH 6.5–7.5, and preferably 7.2, prior to sterilization.

When growth is carried out in shake flasks or large vessels and tanks, it is preferable to use the vegetative form, rather than the spore form, of the microorganism for inoculation to avoid a pronounced lag in the production of Marcfortine B and the attendant inefficient utilization of the equipment. Accordingly, it is desirable to produce a vegetative inoculum in an aqueous nutrient medium by inoculating this medium with an aliquot from a soil or a slant culture. When a young, active vegetative inoculum has thus been secured, it is transferred aseptically to other shake flasks or tanks. The medium in which the vegetative inoculum is produced can be the same as, or different from, that utilized for the production of Marcfortine B, as long as it is such that adequate growth of the microorganism is obtained.

A variety of procedures can be employed to isolate and purify the Marcfortine A from the fermentation broth, for example, by chromatographic adsorption procedures followed by elution with a suitable solvent, column chromatography, partition chromatography, and crystallization from solvents and combinations thereof.

In the preferred recovery process, the Marcfortine B is extracted from the whole beer. Column chromatography techniques, preferably over silica gel, are used to perform the initial purification. Final purification of marcfortine B is achieved by chromatography and crystallization from organic solvents.

Procedure A further illustrates the biotransformation process of the subject invention.

The instant compounds of this invention are unexpectedly potent antiparasitic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition, are also active against Dirofilaria in dogs, Nematospiroides and Syphacia in rodents, biting insects and migrating dipterous larvae such as Hypoderma sp. in cattle, and Gastrophilus in horses.

The instant compounds are also useful against endo and ecto parasites which cause parasitic diseases in humans. Examples of such endoparasites which infect man include gastro intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans. The instant compounds when administered orally or parenterally are administered at a dosage rate of from 0.05 to 20 mg/kg of animal body weight.

The instant compounds are also useful against common household pests such as Blatella sp. (cockroach), Tineola sp. (clothes moth), Attagenus sp. (carpet beetle), *Musca domestica* (housefly) and against *Solenopsis Invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematocide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or drench bolus form or alternatively they can be mixed in the animals feed. The capsules, tablets, and drenches boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, suspending agent, and/or binders such that a uniform mixture solution or suspension is obtained. An inert ingredient is one that will not react with the instant compounds and which is non toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 20% by weight of the active ingredient Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 20% by weight of the active ingredient are acceptable. Preferred formulations are those containing from 0.5 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.005 to 50 mg per kg of animal body weight either in a single dose or in several doses spaced a few days apart generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds-are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention.

EXAMPLE 1

Production and Isolation of Marcfortine A

Seed Fermentation Process:

Seed fermentations are inoculated using agar plugs of isolate Penicillium sp. UC 7780 (NRRL 18887) stored over liquid nitrogen. Three plugs are thawed and used as inoculum. GS-7 is composed of glucose and cottonseed flour (sold under the trademark "Pharmamedia" by Traders Protein, Procter & Gamble Oilseed Products Co., Memphis, Tenn., U.S.A.). Unsupplemented tap water is used to hydrate the medium components and the medium is adjusted to pH 7.2 with $NH_4OH$. The medium is dispensed into unbaffled closed-system flasks at 300 ml pper 1000 ml flask, and sterilized by autoclaving at 121° C. for 30 minutes. Each closed-system flask containing 300 ml of GS-7 medium is inoculated with three agar plugs of Penicillium sp. UC 7780 (NRRL 18887) and shaken on a rotary shaker at 250 rpm for 36 hr at 22° C.

Secondary Seed Fermentation Process:

The mature seed cultures are used as inoculum for the secondary medium at a 0.3% seed rate. The secondary medium is composed of glucose monohydrate (sold as under the trademark Cerelose by C.P.C. International) 25 g, cottonseed flour (sold under the trademark "Pharmamedia") 25 g, $MgCl_2.6H_2O$ 329.8 mg, $MnSO_4.H_2O$ 11.4 mg, $FeSO_4.7H_2O$ 3.2 mg, $Na_2MoO_4.2H_2O$ 1.8 mg, $CaCl_2.2H_2O$ 367.6 mg, NaCl 84.2 mg, KCl 5.8 mg, $ZnSO_4.7H_2O$ 0.1 mg, $CoCl_2.6H_2O$ 0.1 mg, $CuSO_4.5H_2O$ 3.1 mg, and silicone antifoam (sold under the trademark SAG-471 Antifoam) 0.5 ml per liter of reverse-osmosis grade water. Medium components sufficient for 200 liters of secondary seed medium are hydrated in reverse-osmosis grade water to a q.s. volume of 190 liters in a 250-L fermentor. After formulation, the pH of the medium is adjusted to pH 7.2 with $NH_4OH$, and then the medium is sterilized at 121° C. for 30 minutes. Two closed-system flasks of the mature primary-seed culture are used as inoculum at a 0.3% seed rate. The secondary seed culture is incubated at at 22° C., with 125 slm aeration, 5 psig backpressure, and 250 rpm for 36 hours.

Production Fermentation Process:

The production medium is composed of beet molasses 50 g, fish meal (sold under the trademark Menhaden Select Fish Meal) 16 g, yeast extract (sold under the trademark Fidco) 10 g, $MgCl_2.6H_2O$ 329.8 mg, $MnSO_4.H_2O$ 11.4 mg, $FeSO_4.7H_2O$ 3.29 mg, $Na_2MoO_4.2H_2O$ 1.8 mg, $CaCl_2.2H_2O$ 367.6 mg, NaCl 84.2 mg, KCl 5.8 mg, $ZnSO_4.7H_2O$ 0.1 mg, $CoCl_2*6H_2O$ 0.1 mg, $CuSO_4.5H_2O$ 3.1 mg, and silicone antifoam (sold under the trademark SAG-471 Antifoam) 0.5 ml per liter of reverse-osmosis grade water.

Medium components sufficient for 5,000 liters of medium are hydrated in reverse-osmosis grade water to a q.s. volume of 4,700 liters in a 5,000 L fermentor. After formulation, the pH of the medium is adjusted to pH 7.0 with KOH, and then the medium is sterilized at 123° C. for 30 minutes. The mature secondary-seed culture is used as inoculum at a 1.0% seed rate. The culture is incubated at 22° C., with 2,500 slm aeration, 5 psig backpressure, and 250 rpm for 96 hours.

Isolation of Marcfortine A:

The 4900 L fermentation volume is harvested by passing through a high shear mixer to the harvest vessel. Following transfer, 4% wt./v. of diatomaceous earth and ½ volume of methylene chloride are added. The harvest solution is then filtered using a filter press. The filter cake is washed 2 times with a 10% volume of methylene chloride.

The filtrate obtained is decanted to remove the water (aqueous) phase. The remaining product-rich methylene chloride phase is then concentrated to a volume of 44 L. The concentrate is then polished using a 20% concentrate volume (9 L) of methylene chloride and diatomaceous earth over a filter.

The 53 L polished concentrate is further purified to separate Marcfortine A from other components by silica gel chromatography and crystallization.

Before chromatography, the polished concentrate is divided into four approximately equal aliquots. Each aliquot is chromatographed over a newly packed 9" diameter column prepared from 25 Kg of dry silica gel (bed volume 59 L). The loaded columns are eluted with 120 L of 10% acetone in methylene chloride, 120 L of 20% acetone in methylene chloride, 120 L of 30% acetone in methylene chloride, 160 L of 40% acetone in methylene chloride, and 130 L of acetone collecting the 30 and 40% eluates as 20 L fractions. Eluates are monitored by TLC, using for example a solvent system comprised of 6% isopropanol and 0.3% ammoniumn hydroxide in methylene chloride to develop Whatman LK6DF silica gel plates. Fractions of Marcfortine A (containing a small amount of Marcfortine D which co-chromatographs with D) are crystallized from acetone. Appropriate fractions (40–100 L) are concentrated under reduced pressure to a volume of approximately 5 L. The solution (or light slurry) is then transferred to a rotatory evaporater and concentration continued under reduced pressure. Several 1 L portions of acetone are added during the course of the concentration until the methylene chloride is completely displaced. The resulting acetone slurry (approximately 1 L volume) is refrigerated overnight, and the crystals of Marcfortine A are collected and washed with several small portions of cold acetone, and dried under vacuum. Such crystals may be contaminated with several percent of Marcfortine D. Repeated recrystallization from methylene chloride/acetone (displacing methylene chloride as described) affords pure Marcfortine A.

EXAMPLE 1A

Production and Isolation of Marcfortines A and C

Primary Seed Fermentation Process:

Seed fermentations are inoculated using agar plugs of isolate Penicillium sp. UC 7780 (NRRL 18887) stored over liquid nitrogen. Three plugs are thawed and used as inoculum for 100 ml of GS-7 seed medium. GS-7 is composed of glucose and cottonseed flour (sold under the trademark "Pharmamedia" by Traders Protein, Procter & Gamble Oilseed Products Co., Memphis, Tenn., U.S.A.) each added at a concentration of 25 g/L of tap water. After formulation, the pH of GS-7 is adjusted to 7.2 using $NH_4OH$. The medium is autoclaved in 100 ml volumes in 500 ml unbaffled fermentation flasks for 30 min. Sterile GS-7 is inoculated as described above and shaken at 250 rpm for 35–58 hr at 23° C.

Production Fermentation Process (shaker flask):

The mature seed cultures are used as inoculum for the production medium at a 1% seed rate. The production medium is composed of glucose 45 g, enzymatically digested casein (sold under the trademark Peptonized Milk Nutrient by Sheffield Products, Norwich, N.Y., U.S.A.) 25 g, yeast extract (sold under the trademark BACTO Yeast Extract Code: 0127 by Difco Laboratories, Detroit, Mich.) 2.5 g per liter of tap water. After formulation, the pH of the production medium is adjusted to 7.0 using potassium hydroxide. This medium is then autoclaved for 30 min in 100 ml volumes contained in 500 ml baffled fermentation flasks. Sterile production medium is inoculated as described above, and shaken for 7–14 days at 250 rpm at 21° C.

Production Fermentation Process (Labraferm tanks):

The mature seed cultures are used as inoculum for the sterile production medium at a 0.5% seed rate. The production medium is described above. After pH adjustment to 7.0 using KOH, 10 L of this medium are autoclaved for 90 min in 12 L Labraferm tanks (New Brunswick Scientific Co., Inc.). The tanks are inoculated at a 0.5% seed rate and stirred at 500 rpm at 20° C. for 5–9 days. The air flow rate is maintained between 10–15 L/min.

Isolation of Marcfortines A and C:

Whole fermentation broth (35 l) is macerated at low speed in a large commercial Waring Blender and then blended with an equal volume of methylene chloride. The mixture is stored overnight under refrigeration and then subjected to centrifugation to break the emulsion. The resulting clear methylene chloride layer is drawn off and evaporated under reduced pressure. A concentrated solution of the residue (37.4 g) in methylene chloride is applied to a column of silica gel (1 Kg) slurry packed in. methylene chloride. The column is eluted with increasing concentrations of acetone in methylene chloride (10%, 20%, 30%, 40%, and 50% acetone). Fractions are monitored by TLC and appropriate fractions evaporated and crystallized from acetone to give Marcfortine A and Marcfortine C.

EXAMPLE 1B

Production and Isolation of Marcfortines A and C
Seed Fermentation Process:

Seed fermentations are inoculated using agar plugs of isolate Penicillium sp. UC 7780 (NRRIL 18887) stored over liquid nitrogen. Three plugs are thawed and used as inoculum for 100 ml of GS-7 seed medium. GS-7 is composed of glucose and cottonseed flour (sold under the trademark "Pharmamedia" by Traders Protein, Procter & Gamble Oilseed Products Co., Memphis, Tenn., U.S.A.) each added at a concentration of 25 g/L of tap water. After formulation, the pH of GS-7 is adjusted to 7.2 using NH40H. The medium is autoclaved in 100 ml volumes in 500 ml unbaffled fermentation flasks for 30 min. Sterile GS-7 is inoculated as described above and shaken at 250 rpm for 35–58 hr at 23° C.

Production Fermentation Process (Shake Flask):

The mature seed cultures are used as inoculum for the production medium at a 1% seed rate. The production medium is composed of glucose 20 g, glycerol 15 ml, cottonseed flour (sold under the trademark "Pharmamedia" by Traders Protein, Procter & Gamble Oilseed Products Co., Memphis, Tenn., U.S.A.) 20 g, soybean meal 10 g, and $K_2HPO_4$ 3 g per liter of tap water. After formulation, the pH of the production medium is adjusted to 6.8 using potassium hydroxide. This medium is then autoclaved for 30 min in 100 ml volumes contained in 500 ml baffled fermentation flasks. Sterile production medium is inoculated as described above, and shaken for 7–14 days at 250 rpm at 21° C.

Production Fermentation Process (Labraferm tanks):

The mature seed cultures are used as inoculum for the sterile production medium at a 0.5% seed rate. The production medium is described above. After pH adjustment to 7.0 using KOH, 10 L of this medium are autoclaved for 90 min in 12 L Labrafern tanks (New Brunswick Scientific Co., Inc.). The tanks are inoculated at a 0.5% seed rate and stirred at 500 rpm at 20° C. for 5–9 days. The air flow rate is maintained between 10–15 L/min.

Isolation of Marcfortines A and C:

Whole fermentation broth (35 l) is macerated at low speed in a large commercial Waring Blender and then blended with an equal volume of methylene chloride. The mixture is stored overnight under refrigeration and then subjected to centrifugation to break the emulsion. The resulting clear methylene chloride layer is drawn off and evaporated under reduced pressure. A concentrated solution of the residue (37.4 g) in methylene chloride is applied to a column of silica gel (1 Kg) slurry packed in methylene chloride. The column is eluted with increasing concentrations of acetone in methylene chloride (10%, 20%, 30%, 40%, and 50% acetone). Fractions are monitored by TLC and appropriate fractions evaporated and crystallized from acetone to give Marcfortine A and Marcfortine C.

EXAMPLE 2

18-thiomarcfortine A (Compound #2)

A solution of 30 mg marcfortine A and 22 mg of 2,4-bis(methoxyphenyl)-1,3-dithia-2,4-diphosphetane-2,4-disulfide (Lawesson's reagent) in 5 ml of toluene is refluxed under nitrogen for 18 hours. The mixture is cooled and the solvent removed under reduced pressure. The residue is subjected to preparative thin layer chromatography on silica gel plates using 10% acetone in methylene chloride as the eluent to give 18-thiomarcfortine A, mp 258°–260° C.

FAB-MS 494($M^+$+H)

Following the general procedure of Example 2 but employing the appropriate marcfortine starting material, there are prepared the following other 18-thiomarcfortine compounds:

1-methyl-18-thiomarcfortine A
1-benzyl-18-thiomarcfortine A
1-ethyl-18-thiomarcfortine B
1-benzyl-18-thiomarcfortine B
18a-ethyl-18-thiomarcfortine B
18a-benzyl-18-thiomarcfortine B
18a-methoxyethoxymethyl-18-thiomarcfortine B
18a-allyl-18-thiomarcfortine B
18a-propargyl-18-thiomarcfortine B
1,18a-bis-ethyl-18-thiomarcfortine B
1,18a-bis-benzyl-18-thiomarcfortine B
18a-ethyl-24-methoxy-18-thiomarcfortine B
18-thiomarcfortine B (Compound #2A)
  FAB-MS 480($M^+$+H)
18a-ethyl-24,25 dihydro-18-thiomarcfortine B
1-propyl-18-thiomarcfortine C
1-benzyl-18-thiomarcfortine C
18a-propyl-18-thiomarcfortine C
18a-benzyl-18-thiomarcfortine C
18a-methoxyethoxymethyl-18-thiomarcfortine C
18a-allyl-18-thiomarcfortine C
18a-propargyl-18-thiomarcfortine C
1,18a-bis-propyl-18-thiomarcfortine C
1,18a-bis-benzyl-18-thiomarcfortine C
18-thiomarrfortine C
1-palmitoyl-18-thiomarcfortine A
1-decanoyl-18-thiomarcfortine A
1-decanoyl-18-thiomarcfortine B

EXAMPLE 3

24,25 dihydro-18-thiomarcfortine A

A mixture consisting of 15 mg of 5% palladium on carbon and 18-thiomarcfortine A (30 mg, 0.06 mmol) in 1 ml of methanol is stirred vigorously under an atmosphere of hydrogen for 45 minutes. The reaction mixture is filtered through Celite® and the filtrate is evaporated under vacuum. Preparative layer chromatography of the residue on a 0.5 mm silica gel plate eluted with 3% methanol in methylene chloride affords 24,25-dihydro 18-thiomarcfortine A.

EXAMPLE 4

24,25-dibromo-24,25-dihydro 18-thiomarcfortine A

A solution of bromine in chloroform (0.4 ml of 12M solution, 0.048 mmol) is added dropwise to a cold (ice bath) solution of 18-thiomarcfortine A (20 mg, 0.04 mmol) in 2 ml of chloroform. The resulting yellow solution is stirred at room temperature for 15 minutes then evaporated under a steam of nitrogen. Preparative layer chromatography of the residue on a 0.5 mm silica gel plate eluted with 2% methanol in methylene chloride affords 24,25-dibromo-24,25-dihydro-18-thiomarcfortine A.

EXAMPLE 5

24-methoxy 24,25-dihydro 18-thiomarcfortine B

A solution of bromine in chloroform (0.6 ml of 0.12M solution, 0.072 mmol) is added dropwise to a cold (ice bath) solution of 18-thiomarcfortine B (28 mg, 0.06 mmol) in 2 ml of chloroform. The resulting yellow solution is stirred at room temperature for 10 minutes then at 0 C. for 20 minutes then evaporated under a stream of nitrogen. The yellow solid residue is dissolved in 2 ml of methanol then 1,8-diazabicyclo[5.4.0]undec-7-ene (DBU, 0.015 ml, 0.10 mmol) is added. The solution is stirred at room temperature for 90 minutes then evaporated under vacuum. Preparative layer chromatography of the residue on a 1.0 mm silica gel plate eluted with 2% methanol in methylene chloride affords 24-methoxy-25-bromo-24,25-dihydro-18-thiomarcfortine B. The 24-methoxy 25-bromo-24,25-dihydro-18-thiomarcfortine B thus obtained is dissolved in 2 ml of dry toluene then tributyltin hydride (0.12 ml, 0.45 mmol) is added. The solution is stirred at 100° C. for 16 hours then evaporated under vacuum. Preparative layer chromatography of the residue on a 2.0 mm silica gel plate eluted with 2% methanol in methylene chloride affords 24-methoxy 24,25-dihydro-18-thiomarcfortine B.

EXAMPLE 6

24-propoxy 24,25-dihydro-18-thiomarcfortine A

Substitution of propanol for methanol in the procedure described above for 24-methoxy 24,25-dihydro-18-thiomarcfortine B (Example 5) and application of the modified procedure to 20 mg of 18-thiomarcfortine A affords an oily residue. Preparative layer chromatography of the crude produce on a 0.5 mm silica gel plate eluted with 2% methanol in methylene chloride affords 24-propoxy-24,25-dihydro-18-thiomarcfortine A.

EXAMPLE 7

1-(dimethylcarbamoyl)-18-thiomarcfortine A

Potassium hydride (50 mg of a 25% oil dispersion) is added to a solution of 18-thiomarcfortine A (15 mg, 0.030 mmol) in 1 ml of dry tetrahydrofuran. The solution is stirred at room temperature for 2 hours then dimethylcarbamoyl chloride (0.028 ml, 0.30 mmol) is added. The mixture is stirred at room temperature for 18 hours then partitioned between 5% aqueous sodium bicarbonate (1 ml) and methylene chloride (1 ml). The layers are separated and the aqueous layer extracted with methylene chloride (2 ml). The combined extracts are dried with magnesium sulfate, filtered, and evaporated under vacuum. Preparative layer chromatography of the residue on a silica gel plate eluted with 25% acetone in hexane affords 1-(dimethylcarbamoyl)-18-thiomarcfortine A.

Following the general procedure of Example 7 but employing the appropriate marcfortine starting material, there are prepared the following other 18-thiomarcfortine compounds:

1-acetoxymethyl-18-thiomarcfortine A
1-diethoxyphosphoryl-18-thiomarcfortine A
1-cyclopropylcarbonyl-18-thiomarcfortine A
1-dimethylsulfamoyl-18-thiomarcfortine A
1-(1-piperidinyl)thiocarbonyl-18-thiomarcfortine A
1-succinoyl-18-thiomarcfortine A
1-(2,4-dinitrobenzenesulfenyl)-18-thiomarcfortine A
1-(4-morpholinosulfenyl)-18-thiomarcfortine A
1-(p-toluenesulfonyl)-18-thiomarcfortine A
1-acetyl-18-thiomarcfortine A
1-methoxycarbonyl-18-thiomarcfortine A
1-(p-toluenesulfonyl)-18-thiomarcfortine B
1-(2,4-dinitrobenzene sulfonyl)-18a-ethyl-24-methoxy-24,25-dihydro
1-(p-bromobenzene sulfonyl)-18-thiomarcfortine C
1-propionyl-18-thiomarcfortine C
1-(4-carbethoxy-1,3-thiazolidinin-3-yl)carbonyl-18-thiomarcfortine A

EXAMPLE 8

1-benzyl-18-thio-marcfortine A

Potassium hydride (75 mg of a 25% oil dispersion) is added to a solution of 18-thio-marcfortine A (15 mg, 0.030 mmol) in 1 ml of dry tetrahydrofuran. The solution is stirred at room temperature for 2 hours then benzyl bromide (0.025 ml, 0.21 mmol) is added. The mixture is stirred at room temperature for 3 hours then partitioned between water (1 ml) and methylene chloride (1 ml). The layers are separated and the aqueous layer extracted with methylene chloride (2 ml). The combined extracts are dried with magnesium sulfate, filtered, and evaporated under vacuum. Preparative layer chromatography of the residue on a 1.0 mm silica gel plate eluted with 3% methanol in methylene chloride affords 1N-benzyl-18-thio-marcfortine A.

Following the general procedure of Example 8 but employing the appropriate marcfortine starting material, there are prepared the following other 18-thiomarcfortine compounds:

1,18a-bis-ethyl-18-thiomarcfortine B;
1-allyl-18-thiomarcfortine A;
1-methoxymethyl-18-thiomarcfortine A;
1-propargyl-18-thiomarcfortine A;
1-benzyl-18a-ethyl-18-thiomarcfortine B;

EXAMPLE 9

*Haemonchus contortus/Trichostrongylus colubriformis*/Jird Assay:

This in vivo assay utilizes jirds infected with two important target parasites of ruminants. *H. contortus* and *T. colubriformis* (anthelmintic-sensitive or -resistant worms can be used). Initially, activity is assessed only against *H. contortus* as described in G. A. Conder et al., J. Parasitol. 76, 168–170 (1990), while follow-up studies examine activity against both species of parasites using the techniques outlined in G. A. Conder et al., J. Parasitol. 77, 621–623 (1991).

The activity is set forth in Table II.

EXAMPLE 10

Following the general procedure of Example 2 but employing the appropriate paraherquamide/ thioparaherquamide starting material, there are prepared the following other 18-thioparaherquamide compounds:
18-thioparaherquamide
1-methyl-18-thioparaherquamide
1-ethyl-18-thioparaherquamide
1-benzyl-18-thioparaherquamide
1-palmitoyl-18-thioparaherquamide
1-decanoyl-18-thioparaherquamide

EXAMPLE 10a

Following the general procedure of Example 7 but employing the appropriate thioparaherquarmide starting material, there are prepared the following other 18-thioparaherquamide compounds:
1-acetoxymethyl-18-thiomarcfortine
1-diethoxyphosphoryl-18-thioparaherquamide
1-cyclopropylcarbonyl-18-thioparaherquamide
1-dimethylsulfamoyl-18-thioparaherquamide
1-(1-piperidinyl)thiocarbonyl-18-thioparaherquamide
1-succinoyl-18-thioparaherquamide
1-(2,4-dinitrobenzenesulfenyl)-18-thioparaherquamide
1-(4-morpholinosulfenyl)-18-thioparaherquamide
1-(p-toluenesulfonyl)-18-thioparaherquamide
1-acetyl-18-thioparaherquamide
1-methoxycarbonyl-18-thioparaherquamide

EXAMPLE 11

Following the general procedure of Example 8 but employing the appropriate parmherquamide starting material, there are prepared the following other 18-thioparaherquamide compounds:
1,18a-bis-ethyl-18-thioparaherquamide;
1-allyl-18-thioparaherquamide;
1-methoxymethyl-18-thioparaherquamide;
1-propargyl-18-thioparaherquamide;
1-benzyl-18a-ethyl-18-thioparaherquamide.

EXAMPLE 12

1-pyrrolidinylcarbonyl-marcfortine A, Cpd #12

Potassium hydride (50 mg of a 25% oil dispersion) is added to a solution of marcfortine A (15 mg, 0.030 mmol) in 1 ml of dry tetrahydrofuran. The solution is stirred at room temperature for 2 hours then pyrrolidinylcarbonyl chloride (40 mg, 0.30 mmol) is added. The mixture is stirred at room temperature for 18 hours then partitioned between 5% aqueous sodium bicarbonate (1 ml) and methylene chloride (I ml). The layers are separated and the aqueous layer extracted with methylene chloride (2 ml). The combined extracts are dried with magnesium sulfate, filtered, and evaporated under vacuum. Preparative layer chromatography of the residue on a silica gel plate eluted with 25% acetone in hexane affords 1-pyrrolidinyl carbonyl-marcfortine A. $^1$H NMR(CDCl$_3$) δ0.83(s,3H), 1.21(s,3H), 1.41 (s,3H), 1.45(s,3H), 1.3–2.4(m,17H), 2.38(d,1H), 2.6–2.8(m, 2H), 2.84(d,1H), 3.00(s,3H), 3.4–3.6(m,4H), 3.72(d,1H), 4.85(d,1H), 6.41(d,1H), 6.84(s,2H)

Following the general procedure of Example 12 but employing the appropriate marcfortine starting material and carbonyl chloride, there are prepared the following other marcfortine compounds:

1-diethoxyphosphoryl-marcfortine A
1-cyclopropylcarbonyl-marcfortine A, Cpd #12A. $^1$H NMR (CDCl$_3$) δ 0.82(s,3H), 1.05(s,3H), 1.44(2s,6H), 0.9–1.7 (m,8H), 1.7–3.0(m, 11H), 3.14(s,3H), 3.80(d,1H), 4.84(d, 1H), 6.28(d,1H), 6.88(s,2H)
1-(1-piperidinyl)thiocarbonyl-marcfortine A
1-succinoyl-marcfortine A
1-phenoxycarbonyl-marcfortine A, Cpd #12B. $^1$H NMR (CDCl$_3$) δ 0.83(s,3H), 1.09(s,3H), 1.3–1.5(m,1H), 1.42(s, 3H), 1.46(s,3H), 1.5–3.0(m,13H), 3.14(s,3H), 3.70(d,1H), 4.83(d,1H), 6.27(d,1H), 6.90(s,2H), 7.2–7.5(m,5H)
1-(2,4-dichlorophenoxycarbonyl)-18a-allyl-marcfortine B
1-(4-oxopentanoyl)-18a-methyl-marcfortine C
1-palmitoyl-marcfortine A, Cpd #12C
FAB-MS 716(M$^+$+H)
1-(4-nitrophenoxycarbonyl)-marcfortine A, Cpd #12D. $^1$H NMR(CDCl$_3$) δ 0.90(s,3H), 1.09(s,3H), 1.3–1.5(m,1H), 1.44(s,3H), 1.47(s,3H), 1.5–2.9(m,13H), 3.14(s,3H), 3.70 (d,1H), 4.86(d,1H), 6.23(d,1H), 6.93(AB$_q$,2H), 7.48(d, 2H), 8.32(d,2H)
1-(1-piperidinecarbonyl)-marcfortine A, Cpd #12F
FAB-MS 589 (M$^+$+H); HRMS m/z (M$^+$+H, C$_{34}$H$_{44}$N$_4$O$_5$+H$_1$) calc 589.3390, obsd 589.3398
1-[[s(ethoxycarbonyl)piperazin-1-yl]carbonyl]-marcfortine A, Cpd #12G
FAB-MS 662 (M$^+$+H); 684 (M$^+$+Na); HRMS m/z (M$^+$+H, C$_{36}$H$_{47}$N$_5$O$_7$+H$_1$), calc 662.3553, obsd 662.3569
1-[[4-(benzyl)piperazin-1-yl]carbonyl]-marcfortine A, Cpd #12H
$^1$H NMR (300 mHz, CDCl$_3$): 0.80 (s,3H), 1.26 (s,3H), 1.41 (s,3H), 1.45 (s,3H), 1.2–2.9 (m, H), 2.98 (s,3H), 3.4–3.8 (m,8H), 6.41 (d,1H), 6.84 (s,2H), 7.2–7.5 (m,5H). FAB-MS 680 (M$^+$+H); 702 (M$^+$+Na)
1-[[4-(1,3-benzodioxol-5-ylmethyl)piperazin-1-yl]carbonyl]-marcfortine A, Cpd #12I
$^1$H NMR (300 mHz, CDCl$_3$): 0.80 (s,3H), 1.00–2.60 (m,15H), 1.2 (s,3H), 1.41 (s,3H), 1.45 (s,3H), 2.63 (t,1H),2.84 (d,1H), 2.98 (s,3H), 3.45–3.80 (m,8H), 4.85 (d,1H), 5.95.(s,2H), 6.41 (d,1H), 6.70–6.90 (m,5H)
FAB-MS 724 (M$^+$+H)
1-[[4-(methyl)piperazin-1-yl]carbonyl]-marcfortine A, Cpd #12J
$^1$H NMR (300 mHz, CDCl$_3$): 0.82 (s,3H), 1.26 (s,3H), 1.40–2.72 (m,20H), 1.41 (s,3H), 1.44 (s,3H), 2.82 (d,1H), 2.99 (s,3H), 3.40–3.81 (m,5H), 4.85 (d,1H), 6.41 (d,1H), 6.84 (s,2H). FAB-MS 604 (M$^+$+H); HRMS m/z (M$^+$+H, C$_{34}$H$_{45}$N$_5$O$_5$+H$_1$), calc 604.3499, obsd 604.3506
1-(1,3-dihydro-1,3-dioxo-2H-isoindol-2-yl)-marcfortine A, Cpd #12K
FAB-MS 665 (M$^+$+H)
1-1[[4-pyridin-2-yl)piperazin-1-yl]carbonyl]-marcfortine A, Cpd #12L
$^1$H NMR (300 mHz, CDCl$_3$): 0.84 (s,3H), 1.10–2.30 (m,12H), 1.41 (s,3H), 1.44 (s,3H), 2.40 (d,2H), 2.67 (t,2H), 2.85 (d,1H), 3.00 (s,3H), 3.45–3.85 (m,9H), 4.85 (d,1H), 6.40 (d,1H), 6.60–6.70 (m,2H), 6.85 (s,2H), 7.52 (t,1H), 8.15–8.22 (m,1H). FAB-MS 667 (M$^+$+H)
1-[[4-(phenyl)piperazin-1-yl]carbonyl]-marcfortine A, Cpd #12M
$^1$H NMR (300 mHz, CDCl$_3$): 0.84 (s,3H), 1.20–2.50 (m,11H), 1.22 (s,3H), 1.42 (s,3H), 1.45 (s,3H), 2.67 (t,1H), 2.85 (d,1H), 3.00 (s,3H), 3.10–3.91 (m,9H), 4.85 (d,1H), 6.40 (d,1H), 6.85 (s,2H), 6.90–7.00 (m,3H), 7.25–7.38 (m,2H)

1-[[4-(chlorocarbonyl)piperazin-1-yl]carbonyl]-marcfortine A, Cpd #12N $^1$H NMR (300 mHz, CDCl$_3$): 0.74 (s,3H), 1.18 (s,3H), 1.30–2.65 (m,20H), 2.74 (d,1H), 2.81 (s,3H), 3.48–3.90 (m,8H), 4.30 (d,1H), 6.32 (d,1H), 6.80 (s,2H).

FAB-MS 652 (M$^+$+H)

10,10''-(1,4-dicarbonylpiperazine)bis(6',7',8',9',10',10'a-hexahydro-1',1',4,4, 12'-pentamethyl)-[2'S-[2'.alpha, 3'a.alpha,9'a.alpha,10(2'''R*,3'''aS*9'''.aS*,10'''aR*), 10'a.beta,]]-Spiro[4H,8H-[1,4]dioxepino[2,3-g]indole-8, 2'(3'H)-[1H,4H-3a,9a](iminomethano)(cyclopenta[b]quinolizin]-9,11'(10H)-dione, Cpd #12O

FAB-MS 1093(M$^+$+H)

1-[[4-(phenyl)piperidin-1-yl]carbonyl]-marcfortine A, Cpd #12P $^1$H NMR (300 mHz, CDCl$_3$): 0.76 (s,3H), 1.10–2.30 (m,13H), 1.14 (s,3H), 1.35 (s,3H), 1.38 (s,3H), 2.33 (d,1H), 2.52–3.00 (m,8H), 3.00–3.20 (m,1H), 3.50–3.75 (m,2H), 4.05 (d,1H), 4.33 (d,1H), 4.79 (dd, 1H), 6.35 (dd,1H), 6.78 (s,2H), 7.10–7.30 (m,5H).

FAB-MS 665 (M$^+$+H)

1-[[4-(dimethyl)piperidin-1-yl]carbonyl]-marcfortine A, Cpd #12Q $^1$H NMR (300 mHz, CDCl$_3$): 0.75 (s,3H), 0.90–1.95 (m,13H), 0.92 (s,3H), 0.96 (s,3H), 1.14 (s,3H), 1.34 (s,3H), 1.37 (s,3H), 2.08 (d,1H), 2.20 (brs.,1H), 2.33 (d,1H), 2.60 (t,2H), 2.77 (d,1H), 2.92 (s,3H), 3.45–3.75 (m,4H), 4.77 (d,1H), 6.33 (d,1H), 6.77 (s,2H). FAB-MS 617 (M$^+$+H)

1-[[4-(5-chloropyridazin-3-yl)piperazin-1-yl]carbonyl]-marcfortine A, Cpd #12R $^1$H NMR (300 mHz, CDCl$_3$): 0.83 (s,3H), 1.20–2.30 (m,11H), 1.22 (s,3H), 1.42 (s,3H), 1.44 (s,3H), 2.45 (d,1H), 2.65 (t,2H), 2.83 (s,1H), 2.99 (s,3H), 3.60–3.85 (m,8H), 4.86 (d,1H), 6.40 (d,1H), 6.86 (s,2H), 6.92 (d,1H), 7.29 (d,1H).

FAB-MS 702 (M$^+$+H)

1-[[4-(4-chlorophenyl)piperazin-1-yl]carbonyl]-marcfortine A, Cpd #12S $^1$H NMR (300 mHz, CDCl$_3$): 0.84 (s,3H), 1.20–2.30 (m,9H), 1.26 (s,3H), 1.42 (s,3H), 1.45 (s,3H), 2.40 (d,1H), 2.60–2.75 (m,2H), 2.85 (d,1H), 3.00 (s,3H), 3.15–3.30 (m,4H), 3.49 (d,1H), 3.52–3.84 (m,5H), 4.85 (d,1H), 6.39 (d,1H), 6.80–6.90 (m,4H), 7.23 (d,2H).

10,10''-(1,4-dioxo-2-butene)bis(6',7',8',9',10',10'a-hexahydro-1',1',4,4,12'-pentamethyl)-[2'S-[2'.alpha, 3'a.alpha,9'a.alpha,10(2'''R*,3'''aS*9'''aS*, 10'''aR*), 10'a.beta,]]-Spiro[4H,8H-[1,4]dioxepino[2,3-g]indole-8, 2'(3'H)-[1H,4H-3a,9a](iminomethano)cyclopenta[b]quinolizin]-9,11'(10H)-dione, Cpd #12T

FAB-MS 1035(M$^+$+H)

1-[[4-(trichloroethoxycarbonyl)piperazin-1-yl]carbonyl]-marcfortine A, Cpd #12U $^1$H NMR (300 mHz, CDCl$_3$): 0.75 (s,3H), 1.1–1.85 (m,8H), 1.15 (s,3H), 1.34 (s,3H), 1.34 (s,3H), 1.92 (d,1H), 2.00–2.40 (m,2H), 2.34 (d,1H), 2.55 (t,2H), 2.76 (d,1H), 2.91 (s,3H), 3.42–3.75 (m,8H), 4.65–4.77 (m,2H), 4.79 (d,1H), 6.33 (d,1H), 6.79 (s,2H). FAB-MS 764 (M+H); HRMS m/z (M$^+$+H, C$_{36}$H$_{44}$Cl$_3$N$_5$O$_7$+H$_1$), calc 764.2384, obsd 764.2366

1-[[4-(3-trifluoromethyl-thiadiazol-1-yl)piperazin-1-yl]carbonyl]-marcfortine A, Cpd #12V NMR (300 mHz, CDCl$^3$): 0.83 (s,3H), 1.26 (s,3H), 1.30–2.30 (m,11H), 1.42 (s,3H), 1.45 (s,3H), 2.42 (d,1H), 2.55–2.72 (m,2H), 2.84 (d,1H), 2.99 (s,3H), 3.60–3.90 (m,8H), 4.87 (d,1H), 6.30 (d,1H), 6.88 (s,2H). FAB-MS 742 (M$^+$+H); HRMS m/z (M$^+$+H, C$_{36}$H$_{42}$F$_3$N$_7$S$_1$+H$_1$), calc 742.2998, obsd 742.3038

EXAMPLE 13

1-acetoxymethyl-marcfortine A, Cpd #13

Sodium hydride (47 mg of a 60% oil dispersion) is added to a solution of marcfortine A (850 mg, 1.78 mmol) in 1 ml of dry tetrahydrofuran. The solution is stirred at room temperature for 3 hours then methyl bromoacetate (280 mg, 1.82 mmol) is added. The mixture is stirred at room temperature for 4 hours then additional methyl bromoacetate (280 mg, 1.82 mmol) is added. The mixture is stirred at room temperature for 8 hours then partitioned between 5% sodium bicarbonate (1 ml) and methylene chloride (1 ml). The layers are separated and the aqueous layer is extracted with methylene chloride (2 ml). The combined extracts are dried with magnesium sulfate, filtered, and evaporated under vacuum. Column chromatography of the residue on silica gel plate eluting first with 5% then 10% acetone in methylene chloride affords 1 acetoxymethyl-marcfortine A as a colorless oil: $^1$H NMR (CDCl$_3$) δ0.75 (3H, s), 1.08 (3H; s), 1.43 (3H, s), 1.45 (3H, s), 2.05 (3H, s), 3.12 (3H, s), 4.86 (1H, d, J=8), 5.85 (1H, d, J=8), 5.96 (1H, d, J=8), 6.26 (1H, d, J=8), 6.77 (1H, d, J=7), 6.86 (1H, d, J=7).

Following the general procedure of Example 13 but employing the appropriate marcfortine starting material, there are prepared the following other marcfortine compounds:

1-t-butyryloxymethyl-marcfortine A
1-benzoyloxymethyl-marcfortine A
1-acetoxymethyl-18a-benzyl-marcfortine B
1-3,4-dichlorobenzoyloxy-marcfortine C

EXAMPLE 14

1-(2,4-dinitrobenzenesulfenyl)-marcfortine A, Cpd #14

Marcfortine A (75 mg, 0.15 mmol) is added to a suspension of potassium hydride (180 mg, 1.50 mmol, 35 wt % in mineral oil) in THF (6 mL) at 5° C., followed by 2,4-dinitrobenzene-sulfenyl chloride (73 mg, 0.30 mmol). The reaction mixture is then stirred for 3h at 5° C. After diluting with H$_2$O and extracting with CHCl$_3$, the crude product is chromatographed on a 1 mm silica gel preparative thin layer plate eluting with 30% Acetone in methylene chloride to yield 1-(2,4-dinitrobenzenesulfenyl)-marcfortine A (90 mg, 89.1%) as a yellow solid, mp 155°–160° C. (dec). $^1$H NMR (CDCl$_3$): δ0.86–0.97 (m,3H), 1.13–1.45 (m 15H), 1.56–1.78 (m,5H), 1.86 (m,1H), 2.00 (m,1H), 2.15 (d,1H), 2.30 (m,1H), 2.45 (d,1H), 2.67 (bd,1H), 2.79 (d,1H), 2.97 (m,1H), 3.08 (s,3H), 3.74 (d,1H), 4.76 (bd,1H), 5.85 (d,11H, 6.87 (d,1H), 6.97 (d,1H), 7.28 (m,0.5H), 7.62 (m,0.5H), 8.36 (dd,1H), 9.16 (d,1H).

Following the general procedure of Example 14 but employing the appropriate marcfortine starting material, there are prepared the following other marcfortine compounds:

1-(4-morpholinosulfenyl)-marcfortine A, Cpd #14A
FAB-MS; m/e, 595(m$^+$+H)
1-(trichloromethylsulfenyl)-marcfortine A, Cpd #14B
FAB-MS; m/e, 626, 628, 630 (M$^+$+H)
1-(methoxycarbonylsulfenyl)-marcfortine A, Cpd #14C)
FAB-MS; m/e, 568 (M$^+$+H)
1-(benzenesulfenyl)-marcfortine A, Cpd #14D FAB-MS; m/e, 586 (M⁺+H)
1-trichloromethylsulfenyl-18a-ethyl-marcfortine B
1-ethoxycarbonylsulfenyl-18a-methyl-marcfortine C

EXAMPLE 15

1-(4-morpholinecarbonyl)-marcfortine A N-oxide, Cpd #15

1-(4-Morpholinecarbonyl)-marcfortine A (Cpd #12E, 15 mg) is treated with 3-chloroperoxybenzoic acid (15 mg) in methylene chloride (2 ml) at 0C for 10 minutes. The mixture is partitioned between 5% sodium bicarbonate (2 ml) and methylene chloride (2 ml). The layers are separated and the aqueous layer is extracted with methylene chloride (2 ml). The combined extracts are dried with magnesium sulfate, filtered and evaporated under vacuum. The residue is chromatographed on a 0.5 mm silica gel preparative thin layer plate eluting with 10% methanol in methylene chloride to yield the title compound (10 mg) as a solid. FAB-MS; 607(M⁺+H)

EXAMPLE 16

1-(2-tetrahydrofaranyl)-marcfortine A, Cpd #16

Carbonyldiimidazole (50 mg) is added to a solution of marcfortine A (60 mg) in 6 ml of tetrahydrofuran. The mixture is heated to reflux and potassium hydride (120 mg) is added. The resulting mixture is stirred under refluxing for 1 hour. The precipitate is filtered off and the filtrate is concentrated. The residue is chromatographed on a silica plate, eluting with 25% acetone in methylene chloride to yield the title compound (30 mg) as a solid. HMS (FAB); m/e(M⁺+H, $C_{32}H_{41}N_3O_5$+H), calc. 548.3124, obsd. 548.3086

EXAMPLE 17

1-(4-morpholinecarbonyl)-marcfortine A, Cpd#12E

Marcfortine A (1 g, 2.1 mmol) in THF (25 mL, distilled from sodium metal and benzophenone) and potassium hydride (35 weight %, 0.5 g, 4.4 mmol) are stirred for 0.5 h at room temperature under nitrogen. Morpholinecarbonyl chloride (1 mL, 8.4 mmol) is then added via syringe. After 3 hr of stirring at room temperature the turbid reaction mixture is cooled in an ice water bath and quenched with dropwise addition of cold saturated potassium-carbonate solution (5 mL). The mixture is then diluted with water (75 mL) and extracted into $CH_2Cl_2$ (175 mL). The organic layer is dried over magnesium sulfate, filtered and concentrated to give the crude material which contains oil. Silica gel chromatography (2% to 5% MeOH/$CH_2Cl_2$) gives 1-morpholinecarbonyl-marcfortine A. (Silica gel chromatography on the chromatotron (4% MeOH/$CH_2Cl_2$) is a better method of purification for 1-morpholinecarbonyl-marcfortine A.) ¹H NMR (300 MHz, $CDCl_3$) δ0.81 (s, 3H), 1.21 (s, 3H), 1.19–1.94 (m, 8H), 1.41 (s, 3H), 1.45 (s, 3H), 1.98 (d, 1H), 2.08–2.28 (m, 2H), 2.40 (d, 1H), 2.62 (t, 2H), 2.82 (d, 1H), 2.99 (s, 3H), 3.50–3.86 (m, 8H), 4.86 (d, 1H), 6.41 (d, 1H), 6.85 (s, 2H). FAB-MS 591 (M⁺+(M⁺+H, $C_{33}H_{42}N_4O_6$+$H_1$), calc. 591.3182, obsd. 591.3200.

EXAMPLE 18

Following the general procedure of Example 12 but employing the appropriate paraherquamide starting material, there are prepared the following other paraherquamide compounds:

1-diethoxyphosphoryl-paraherquamide
1-cyclopropylcarbonyl-paraherquamide
1-(1-piperidinyl)thiocarbonyl-paraherquamide
1-succinoyl-paraherquamide
1-(4-carbethoxy-1,3-thiazolidinin-3-yl)carbonyl-paraherquamide
1-phenoxycarbonyl-paraherquamide
1-pyrrolidinylcarbonyl-paraherquamide
1-piperidinylcarbonyl-paraherquamide
1-(4-morpholinecarbonyl)-paraherquamide

EXAMPLE 19

Following the general procedure of Example 13 but employing the appropriate paraherquamide starting material, there are prepared the following other paraherquamide compounds:

1-t-butyryloxymethyl-paraherquamide
1-benzoyloxymethyl-paraherquamide
1-acetoxymethyl-18a-paraherquamide
1-3,4-dichlorobenzoyloxy-paraherquamide

EXAMPLE 20

Following the general procedure of Example 14 but employing the appropriate paraherquamide starting material, there are prepared the following other paraherquamide compounds:

1-(2,4-dinitrobenzenesulfenyl)-paraherquamide
1-(4-morpholinosulfenyl)-paraherquamide
1-trichloromethylsulfenyl-18a-ethyl-paraherquamide
1-ethoxycarbonylsulfenyl-18a-methyl-paraherquamide
1-palmitoyl-paraherquamide Procedure A:

A. Seed Fermentation

*Cunninghamella echinulata* subsp. elegans (−) NRRL 1368, *Cunninghamella blakesleeana* (+) ATCC 8688a, *Cunninghamelia echinulata* subsp. elegans (−) NRRL 1393, *Cunninghamella echinulata* NRRL 3655

Frozen agar plugs of NRRL 1368 or 1393, ATCC 8688a or preferably NRRL 3655 (stored over liquid nitrogen "$LN_2$") are aseptically transferred into a 100 ml vol of GS-7 (sterile) medium contained in a 500 ml large mouth shake flask. GS-7 is composed of Cerelose and Pharmamedia, each added at 25 g/l of tap water. The pH of the medium is adjusted to pH 7.2 using ammonium hydroxide. The medium is sterilized by autoclaving for 30 min. Inoculated GS-7 is shaken at 125 to 300 (preferably 250 rpm) at 21°–30° C., preferably about 28° C., for 24–72 hrs (preferably about 48–72 hours). This fermentation is used to inoculate the biotransformation process at about 1 to about 5% rate (preferably about 5% rate).

B. Biotransformation Process 100 ml vols of GS-7 contained in 500 ml large mouth fermentation flasks are inoculated with the 48–72 hr seed fermentation at about 1 to about 5% rate (preferably about 5% rate). The inoculated GS-7 is shaken at about 250 rpm at 28° C. for 2448 hrs. At this time Marcfortine A, dissolved in dimethylformamide (DMF), is added to the fermentation in a range between 10–12 mg/flask, preferably at 10 mg per 0.4 ml DMF per 100 ml flask/fermentation. The fermentations containing Marcfortine A are continued as previously indicated for 24–72 hrs.

The contents of 100 flasks, each containing 100 ml fermentation as described in the protocol for biotransformation and which had been shaken at 28° C. for 24–72 hours following addition of Marcfortine A (0.010 g per flask, 1 g total) in DMF (0.2 ml per flask, 20 ml total) are each treated with $CH_2Cl_2$ (100 ml). The contents are combined and stirred in a waring blender for 5 minutes. The mixture is centrifuged and the resulting aqueous layer is decanted. The organic layer is collected, dried (sodium sulfate), filtered and concentrated. The components of the crude mixture are separated by a series of column chromatographies using a silica gel—solid extract ratio of 50–125:1. Columns are eluted with either 2–5% methanol in $CH_2Cl_2$ or 15–60% acetone in $C_2Cl_2$. From these chomatographic separations there is isolated Marcfortine B. HRMS (FAB); mle, found, 464.2563; calculated for $C_{27}H_{33}N_3O_4+H_1$, 464.2549.

If desired, marcfortine B may be crystallized from methylene chloride/acetone. For example, a methylene chloride solution of marcfortine B is concentrated under partial vacuum on a rotatory evaporator. The concentrate is diluted with portions of acetone during the concentration until a slurry of marcfortine B in acetone remains.

TABLE I

Colonial Morphologies of UC 7780

| Medium & Temp | Diameter | Shape | Surface Texture | Mycelium | Margins | Soluble Pigment | Reverse | Additional |
|---|---|---|---|---|---|---|---|---|
| CYA, 24° C. | 22–25 mm | umbonate sulcate | velutinous | white to pale green | entire regular | reddish w/age | beige to salmon red w/age | occasional clear pink exudate |
| MEA, 24° C. | 25–28 mm | flat | floccose | green w/white periphery | irregular | none | beige | |
| G25N, 24° C. | 12–15 mm | umbonate | velutinous | white w/green periphery | regular | none | beige | |
| CYA, 5° C. | no germination | | | | | | | |
| CYA, 37° C. | 5–10 mm | umbonate | velutinous granular | white | irregular | none | beige | |

TABLE II

ANTHELMINTIC JIRD PHASE 2 SCREEN

| CPD # | Dose | | # Animals | # Surviv. | % Red HC | % Red TC |
|---|---|---|---|---|---|---|
| 2 | 1 | MG/JIRD | 3 | 3 | 89 | 100 |
| | 0.33 | MG/JIRD | 3 | 3 | 23 | 96 |
| | 0.11 | MG/JIRD | 3 | 3 | 0 | 0 |
| 2A | 0.33 | MG/JIRD | 3 | 3 | 76 | 98 |
| | 0.11 | MG/JIRD | 3 | 3 | 29 | 72 |
| 12 | 1 | MG/JIRD | 3 | 3 | 100 | 100 |
| | 0.33 | MG/JIRD | 3 | 3 | 99 | 100 |
| | 0.11 | MG/JIRD | 3 | 3 | 73 | 0 |
| | 0.037 | MG/JIRD | 3 | 3 | 12 | 30 |
| | 0.11 | MG/JIRD | 2 | 2 | 65 | 61 |
| | 0.037 | MG/JIRD | 3 | 3 | 8 | 0 |
| 12A | 1 | MG/JIRD | 3 | 3 | 99 | 90 |
| | 0.33 | MG/JIRD | 3 | 3 | 28 | 3 |
| 12B | 1 | MG/JIRD | 3 | 3 | 100 | 100 |
| | 0.33 | MG/JIRD | 3 | 3 | 55 | 85 |
| 12C | 1 | MG/JIRD | 3 | 3 | 100 | 100 |
| | 0.33 | MG/JIRD | 3 | 3 | 99 | 100 |
| | 0.11 | MG/JIRD | 3 | 3 | 28 | 43 |
| 12D | 1 | MG/JIRD | 3 | 3 | 94 | 99 |
| | 0.33 | MG/JIRD | 3 | 3 | 51 | 70 |
| 12E | 1 | MG/JIRD | 3 | 3 | 99 | 100 |
| | 0.33 | MG/JIRD | 3 | 3 | 100 | 100 |
| | 0.11 | MG/JIRD | 3 | 3 | 80 | 99 |
| | 0.037 | MG/JIRD | 3 | 2 | 0 | 42 |
| 12F | 1 | MG/JIRD | 3 | 3 | 99 | 100 |
| | 0.33 | MG/JIRD | 3 | 3 | 98 | 100 |
| | 0.11 | MG/JIRD | 3 | 3 | 74 | 78 |
| 12G | 1 | MG/JIRD | 3 | 3 | 99 | 100 |
| | 0.33 | MG/JIRD | 3 | 3 | 95 | 100 |
| | 0.11 | MG/JIRD | 3 | 3 | 0 | 61 |
| 12H | 0.33 | MG/JIRD | 3 | 3 | 99 | 99 |
| | 0.11 | MG/JIRD | 3 | 3 | 2 | 61 |
| 12I | 1 | MG/JIRD | 3 | 3 | 100 | 100 |
| | 0.33 | MG/JIRD | 3 | 3 | 100 | 100 |
| | 0.11 | MG/JIRD | 3 | 2 | 69 | 87 |
| 12J | 1 | MG/JIRD | 3 | 3 | 100 | 100 |
| | 0.33 | MG/JIRD | 3 | 3 | 96 | 96 |
| | 0.11 | MG/JIRD | 3 | 3 | 32 | 99 |
| | 0.037 | MG/JIRD | 3 | 3 | 22 | 44 |
| 12K | 1 | MG/JIRD | 3 | 3 | 100 | 100 |
| | 0.33 | MG/JIRD | 3 | 3 | 66 | 54 |
| 12L | 0.33 | MG/JIRD | 3 | 3 | 99 | 99 |
| | 0.11 | MG/JIRD | 3 | 3 | 37 | 56 |
| 12M | 0.33 | MG/JIRD | 3 | 3 | 97 | 100 |
| | 0.11 | MG/JIRD | 3 | 3 | 73 | 98 |
| | 0.11 | MG/JIRD | 2 | 2 | 25 | 40 |
| | 0.037 | MG/JIRD | 3 | 3 | 11 | 66 |
| 12N | 0.33 | MG/JIRD | 3 | 3 | 100 | 100 |
| | 0.11 | MG/JIRD | 3 | 3 | 81 | 98 |
| | 0.11 | MG/JIRD | 2 | 2 | 0 | 39 |
| | 0.037 | MG/JIRD | 3 | 3 | 62 | 50 |
| 12O | 0.33 | MG/JIRD | 3 | 3 | 100 | 100 |
| | 0.11 | MG/JIRD | 3 | 3 | 80 | 98 |
| | 0.11 | MG/JIRD | 2 | 2 | 46 | 77 |
| | 0.037 | MG/JIRD | 3 | 3 | 39 | 46 |
| 12P | 0.33 | MG/JIRD | 3 | 3 | 100 | 100 |
| | 0.11 | MG/JIRD | 3 | 3 | 51 | 78 |
| 12Q | 0.33 | MG/JIRD | 3 | 3 | 99 | 99 |
| | 0.11 | MG/JIRD | 3 | 3 | 53 | 63 |
| 12R | 0.33 | MG/JIRD | 3 | 3 | 100 | 99 |
| | 0.11 | MG/JIRD | 3 | 2 | 96 | 97 |
| | 0.11 | MG/JIRD | 3 | 3 | 0 | |
| | 0.037 | MG/JIRD | 3 | 3 | 5 | |
| | 0.33 | MG/JIRD | 3 | 3 | 99 | 100 |
| | 0.11 | MG/JIRD | 3 | 3 | 76 | 80 |
| 12S | 0.33 | MG/JIRD | 3 | 3 | 100 | 100 |
| | 0.11 | MG/JIRD | 3 | 3 | 93 | 100 |
| | 0.11 | MG/JIRD | 3 | 3 | 29 | |
| | 0.037 | MG/JIRD | 3 | 3 | 27 | |
| | 0.33 | MG/JIRD | 3 | 3 | 98 | 100 |
| | 0.11 | MG/JIRD | 3 | 3 | 61 | 97 |

TABLE II-continued

ANTHELMINTIC JIRD PHASE 2 SCREEN

| CPD # | Dose  |         | # Animals | # Surviv. | % Red HC | % Red TC |
|-------|-------|---------|-----------|-----------|----------|----------|
| 12T   | 0.33  | MG/JIRD | 3         | 3         | 74       | 93       |
|       | 0.11  | MG/JIRD | 3         | 3         | 32       | 74       |
| 12U   | 0.33  | MG/JIRD | 3         | 3         | 100      | 99       |
|       | 0.11  | MG/JIRD | 3         | 3         | 72       | 82       |
| 12V   | 0.33  | MG/JIRD | 3         | 3         | 98       | 98       |
|       | 0.11  | MG/JIRD | 3         | 3         | 87       | 86       |
| 13    | 1     | MG/JIRD | 3         | 3         | 100      | 100      |
|       | 0.33  | MG/JIRD | 3         | 3         | 55       | 90       |
| 14    | 1     | MG/JIRD | 3         | 3         | 100      | 99       |
|       | 0.33  | MG/JIRD | 3         | 3         | 100      | 100      |
|       | 0.11  | MG/JIRD | 3         | 3         | 74       | 91       |
|       | 0.037 | MG/JIRD | 3         | 3         | 29       | 0        |
|       | 0.33  | MG/JIRD | 3         | 3         | 99       | 100      |
| 14A   | 0.33  | MG/JIRD | 3         | 3         | 96       | 100      |
|       | 0.11  | MG/JIRD | 3         | 3         | 81       | 63       |
| 14B   | 1     | MG/JIRD | 3         | 3         | 100      | 100      |
|       | 0.33  | MG/JIRD | 3         | 3         | 98       | 100      |
|       | 0.11  | MG/JIRD | 3         | 3         | 0        | 76       |
| 14C   | 1     | MG/JIRD | 3         | 2         | 100      | 99       |
|       | 0.33  | MG/JIRD | 3         | 3         | 98       | 100      |
|       | 0.11  | MG/JIRD | 3         | 3         | 29       | 80       |
|       | 0.037 | MG/JIRD | 3         | 3         | 56       | 0        |
| 14D   | 1     | MG/JIRD | 3         | 3         | 100      | 100      |
|       | 0.33  | MG/JIRD | 3         | 3         | 100      | 100      |
|       | 0.11  | MG/JIRD | 3         | 3         | 32       | 67       |
| 15    | 1     | MG/JIRD | 3         | 3         | 99       | 100      |
|       | 0.33  | MG/JIRD | 3         | 3         | 61       | 76       |
| 16    | 1     | MG/JIRD | 3         | 3         | 99       | 100      |
|       | 0.33  | MG/JIRD | 3         | 3         | 92       | 100      |
|       | 0.11  | MG/JIRD | 3         | 3         | 50       | 12       |
|       | 0.33  | MG/JIRD | 3         | 3         | 98       | 100      |
|       | 0.11  | MG/JIRD | 3         | 3         | 76       | 99       |

Compound 2

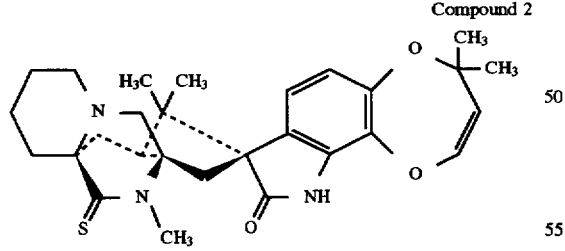

Compound 2A

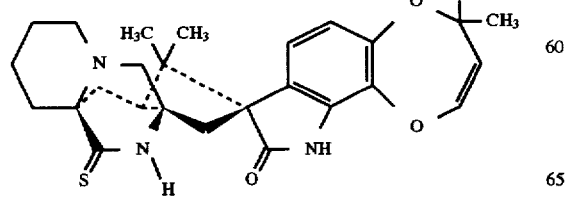

Compound 12

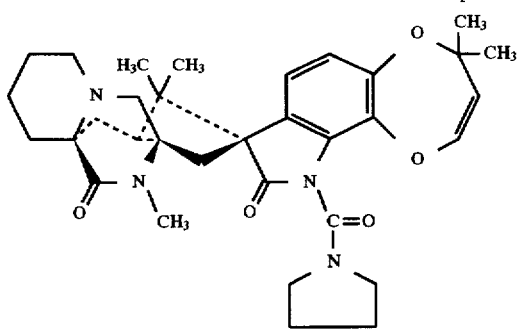

Compound 12A

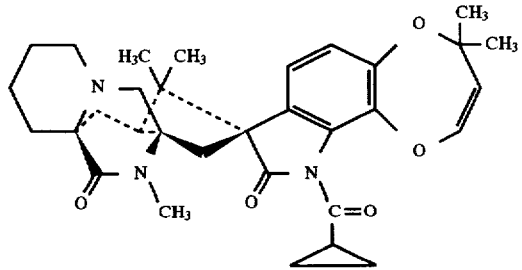

Compound 12B

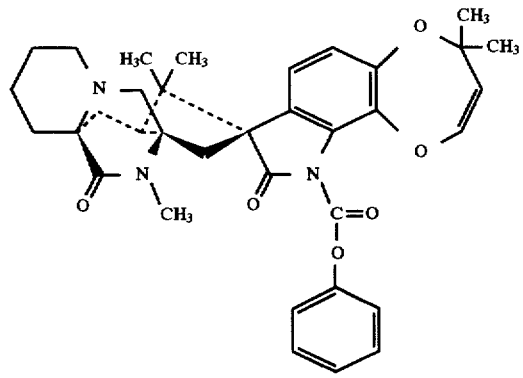

Compound 12C

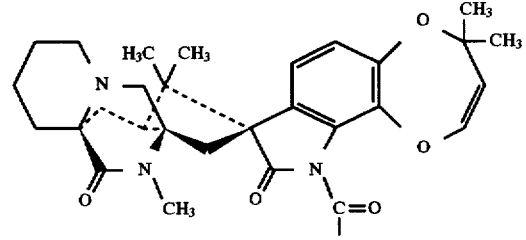

41
-continued
Compound 13
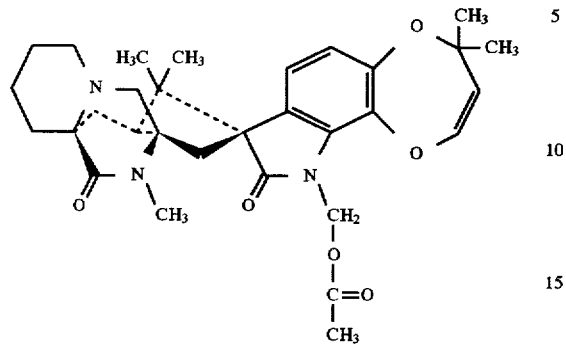
Compound 14
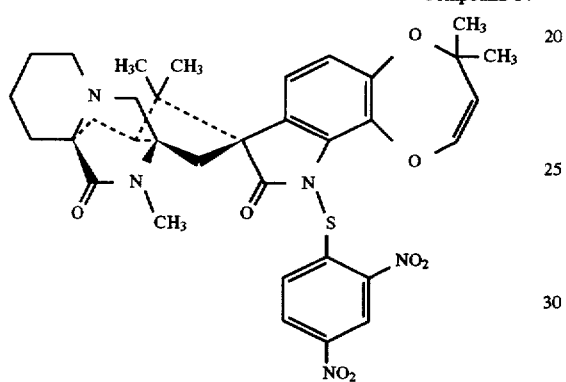
Compound 12D
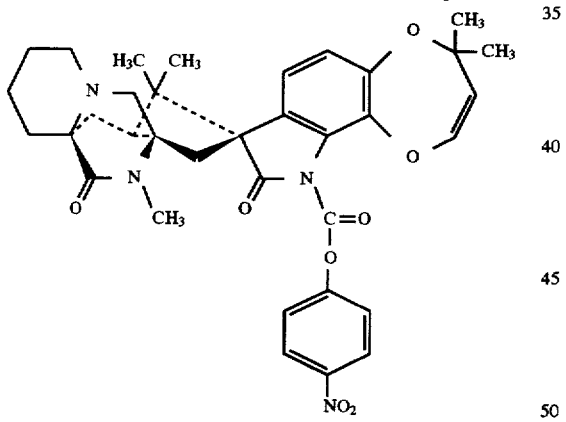
Compound 15
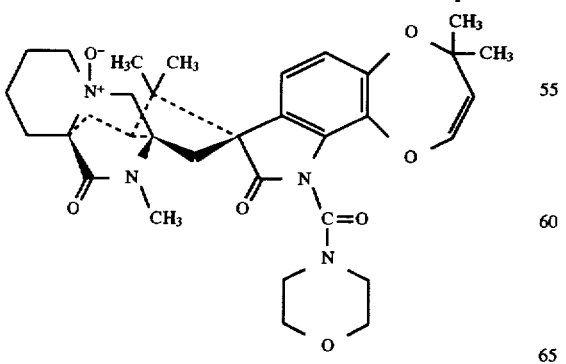
42
-continued
Compound 12E
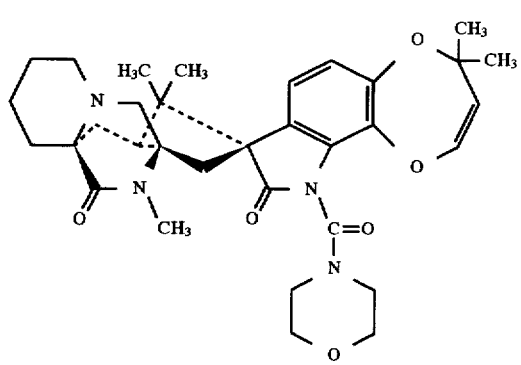
Compound 14B
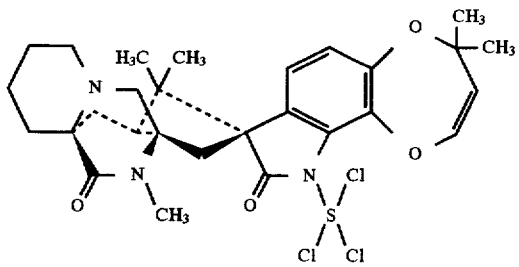
Compound 14D
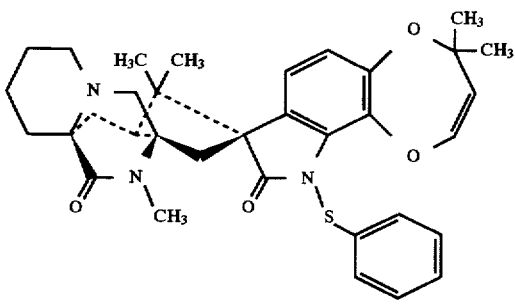
Compound 12F
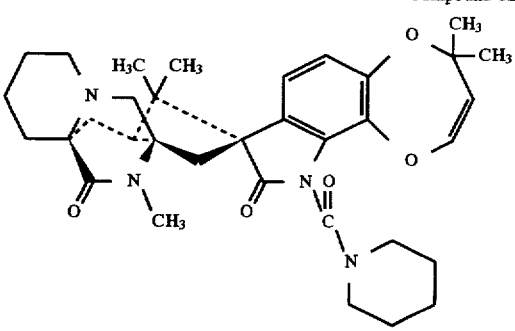

43
-continued
Compound 12G
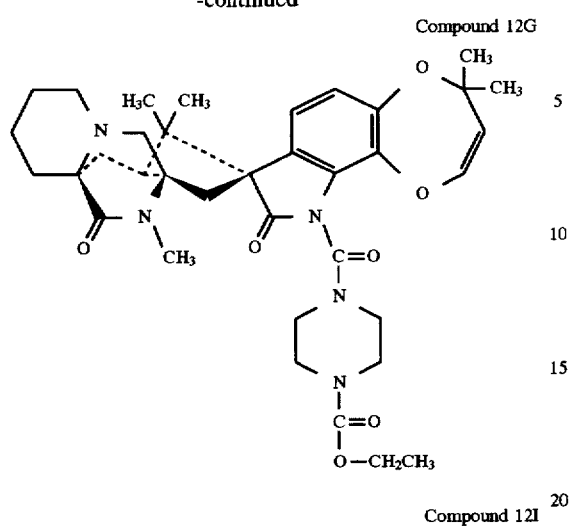
Compound 12I
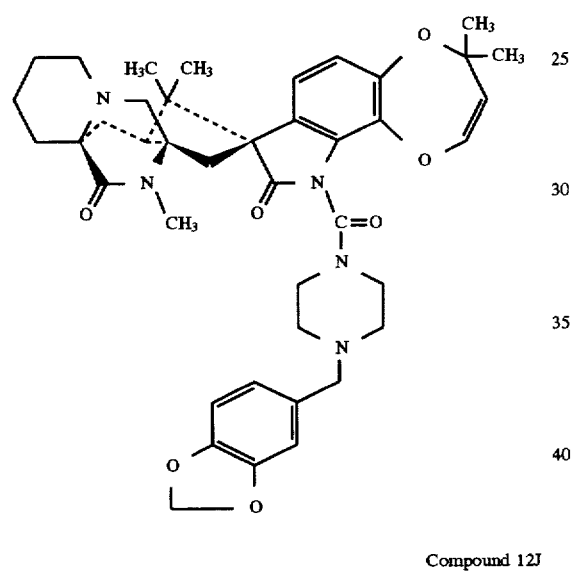
Compound 12J
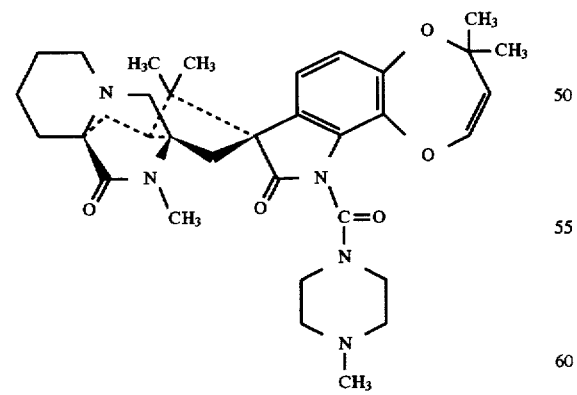
44
-continued
Compound 12K
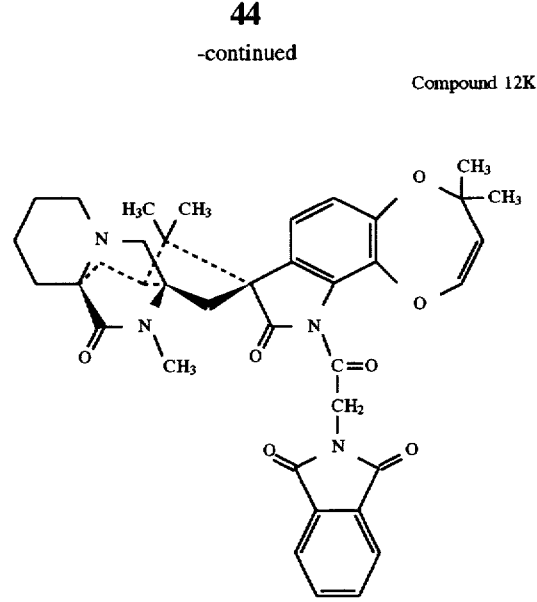
Compound 14C
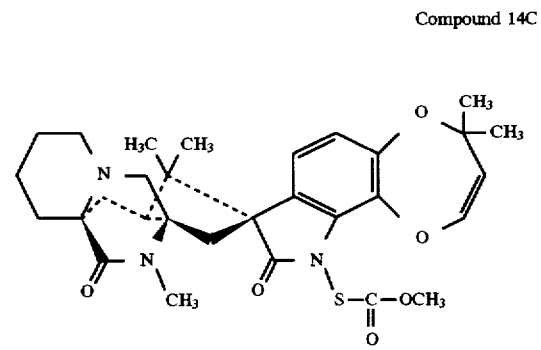
Compound 14A
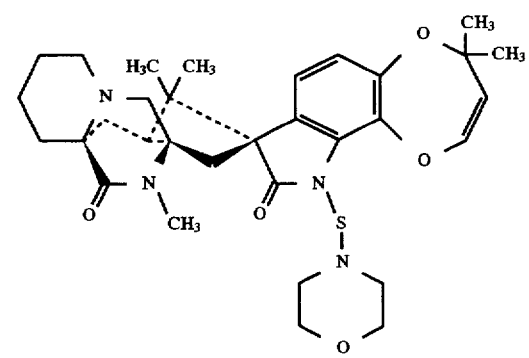

45
-continued
Compound 12L
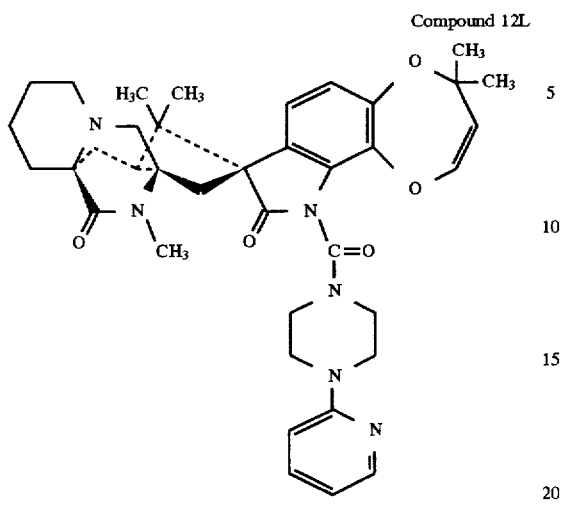
Compound 12M
Compound 12N
46
-continued
Compound 12P
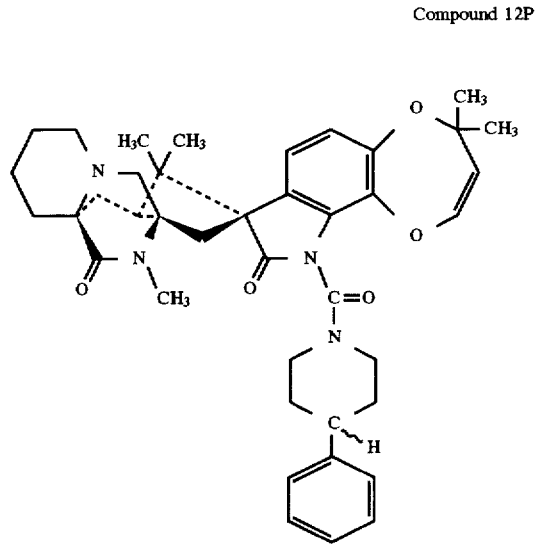
Compound 12Q
Compound 12R Compound 12S
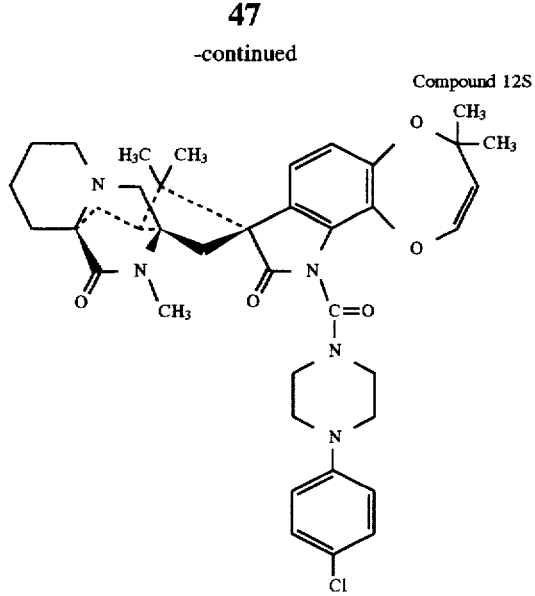
Compound 12U
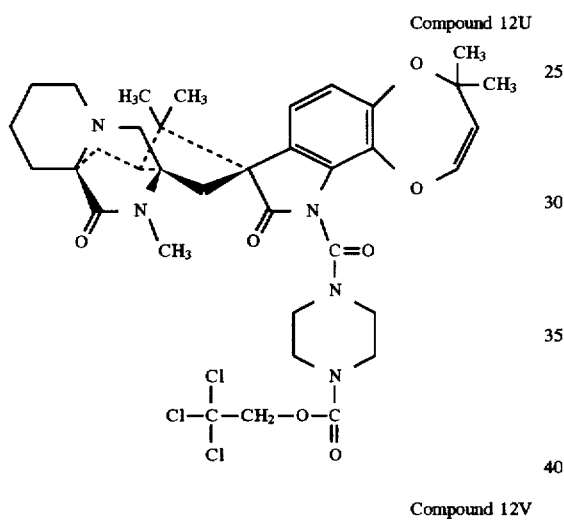
Compound 12V
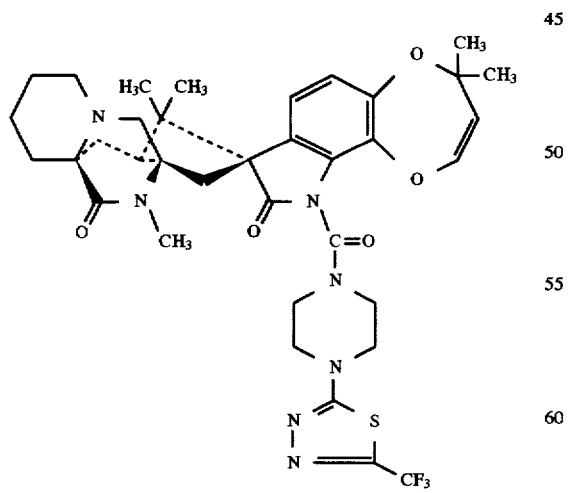
Compound 12H
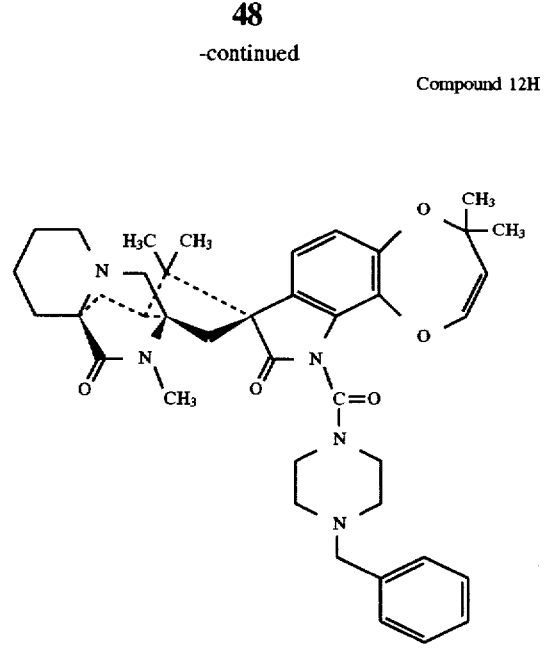
Compound 12O
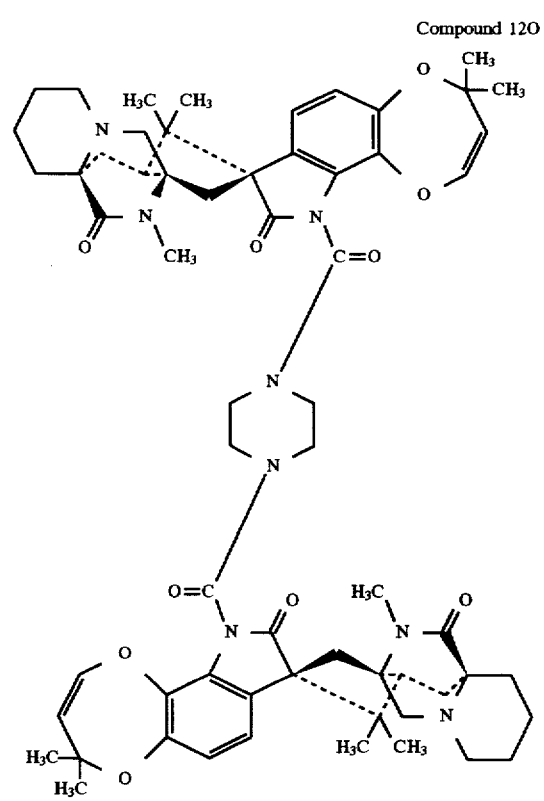

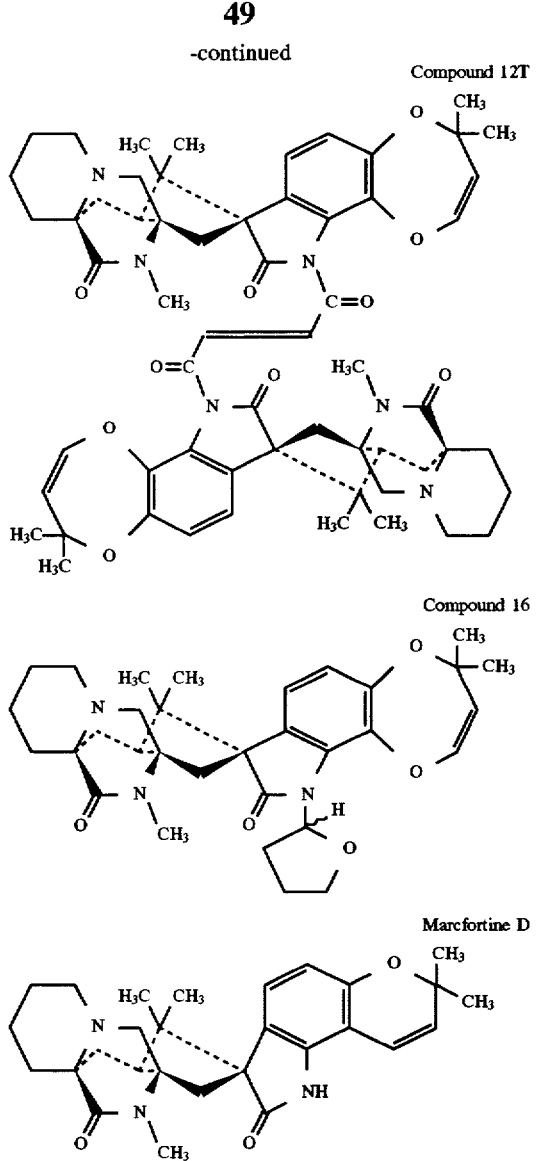

We claim:
1. A compound of Formula I

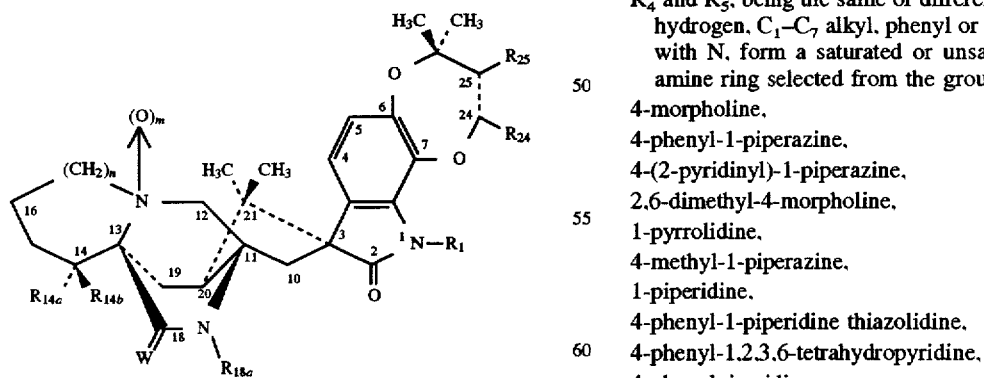

wherein:
n is 0 or 1;
$R_{14a}$ and $R_{14b}$, being the same or different, are selected from hydrogen, hydroxy, $C_1$–$C_6$ alkyl $C_1$–$C_6$ alkoxy, $C_1$–$C_6$ alkenyl, $C_1$–$C_6$ alkenyl-$C_1$–$C_6$ alkoxy, $C_1$–$C_6$ alynyl-$C_1$–$C_6$ alkoxy, $C_1$–$C_6$ alkynoyloxy, poly $C_1$–$C_6$ alkoxy-$C_1$–$C_6$ alkoxy, phenyl, phenyl-$C_1$–$C_6$ alkyl, tri-$C_1$–$C_6$ akylsilyloxy, diphenylphosphoryloxy and halogen, or $R_{14a}$ and $R_{14b}$ together form the epoxide or =$CH_2$, with the proviso that when n is 1, then $R_{14a}$ and $R_{14b}$ are both hydrogen;

m is 0 or 1;

W is O or S;

when W is S, $R_1$ is hydrogen, $C_1$–$C_7$ alkyl, cyclo $C_3$–$C_8$alkyl, benzyl, $C_2$–$C_7$ alkanoyl (—C(O)$C_1$–$C_6$alkyl), $C_{10}$–$C_{24}$alkanoyl (—C(O)$C_9$–$C_{23}$alkyl, cyclo $C_3C_8$alkanoyl, alkanoyloxymethylene (—$CH_2$OC(O)—$C_2$–$C_7$alkyl), benzoyloxymethylene (—$CH_2$OC(O)phenyl), $C_{10}$–$C_{24}$alkenoyl (—C(O) $C_1$–$C_{23}$alkenyl), benzenesulfonyl (—$SO_2$phenyl), di($C_1$–$C_4$alkyl)aminocarbonyl (—C(O)N($C_1$–$C_4$alkyl)$_2$), di($C_1$–$C_4$alkyl)aminothiocarbonyl (—C(S) N($C_1$–$C_4$alkyl)$_2$), $C_1$–$C_7$ alkoxycarbonyl, phenoxycarbonyl, —C(O)NR'$_4$R'$_5$, —P(=X)($R_2$)($R_3$), —$SR_6$, —$SO_2NR_4R_5$, benzoyl substituted at the 3 or 4 position with —$CH_2NR_4R_5$, 2-tetrahydrofuran, or bicyclo$C_8$–$C_{12}$alkanoyl;

when W is O; $R_1$ is selected from the group consisting of:
(a) $C_2$–$C_7$ alkanoyl substituted with carboxy (—COOH), $C_1$–$C_7$ alkanoyl, carbo$C_1$–$C_7$alkoxy (—C(O)O$C_1$–$C_7$alkyl), —$NR_4R_5$, aminocarbonyl (—C(O)$NR_4R_5$);
(b) cyclo $C_3$–$C_8$alkanoyl optionally substituted with carboxy, $C_1$–$C_7$ alkanoyl, carbo$C_1$–$C_7$alkoxy, —$NR_4R_5$, aminocarbonyl;
(c) alkanoyloxymethylene (—$CH_2$OC(O)—$C_2$–$C_7$alkyl);
(d) benzoyloxymethlene (—$CH_2$OC(O)phenyl) substituted with 1 or 2 groups selected from halogen, $C_1$–$C_4$ alkyl, halo$C_1$–$C_7$alkyl, nitro, cyano and $C_1$–$C_7$alkoxy;
(e) phenoxycarbonyl substituted with 1 or 2 groups selected from halogen, $C_1$–$C_4$ alkyl, halo$C_1$–$C_7$alkyl, nitro, cyano and $C_1$–$C_7$alkoxy;
(f) —C(O)NR'$_4$R'$_5$;
(g) —P(=X)($R_2$)($R_3$);
(h) —$SR_6$;
(i) $C_{10}$–$C_{24}$alkanoyl (—C(O)$C_{10}$–$C_{24}$alkyl);
(j) $C_{10}$–$C_{24}$alkenoyl (—C(O)$C_9$–$C_{23}$alkenyl); or
(k) 2-tetrahydrofuran;

$R_4$ and $R_5$, being the same or different, are selected from hydrogen, $C_1$–$C_7$ alkyl, phenyl or when taken together with N, form a saturated or unsaturated heterocyclic amine ring selected from the group consisting of:

4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine thiazolidine,
4-phenyl-1,2,3,6-tetrahydropyridine,
4-phenylpiperidine,
ethyl prolinate,
tetrahydrofurylamine,
3-pyrroline,
thiazolidine-4-carboxylic acid,
thiomorpholine, nipecotamide,
2-methylpiperidine,
3-methylpiperidine,
4-methylpiperidine,
N-methylpiperazine,
1-methylhomopiperazine,
1-acetylpiperazine and
N-carboethoxypiperazine;

$R'_4$ and $R'_5$, being the same or different, are selected from $C_1-C_7$ alkyl, cyclo($C_3-C_8$)alkyl, phenyl or when taken together with N, form a saturated heterocyclic amine ring selected from the group consisting of 4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine thiazolidine,
4-phenyl-1,2,3,6-tetrahydropyridine,
4-phenylpiperidine,
ethyl prolinate,
tetrahydrofurylamine,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine and
N-carboethoxypiperazine;

X is O or S;

$R_2$ and $R_3$, being the same or different, are selected from $C_1-C_7$ alkyl, phenyl, $C_1-C_7$ alkoxy, thio($C_1-C_7$) alkoxy, phenoxy, thiophenoxy, —$NR_7R_8$, or taken together with P form a 4- to 7-membered heterocyclic ring selected from the group consisting of 1,3-dioxa-2-phosphorinane, 1-aza-3-oxa-2-phospholane, 1,3-diaza-2-phospholane and 1-thia-3-oxa-2-phospholane;

$R_6$ is $C_1-C_7$ alkyl, halo$C_1-C_7$alkyl, carbo$C_1-C_7$alkoxy, —$NR_9R_{10}$ where $R_9$ and $R_{10}$, being the same or different, are $C_1-C_7$ alkyl or phenyl $C_7$alkyl, nitro, cyano, $C_1-C_1$ alkoxy);

$R_{24}$ is hydrogen, halogen or $C_1-C_7$ alkoxy;

$R_{25}$ is hydrogen or halogen;

$R_{18a}$ is hydrogen, $C_1-C_7$ alkyl, $C_2-C_8$ alkoxyalkyl, $C_2-C_8$ alkenyl, $C_2-C_8$ alkynyl or benzyl;

the broken line between carbons 24 and 25 represents a single or double bond; and pharmaceutically acceptable salts and hydrates thereof;

with the overall proviso that, when W is O, $R'_4$ and $R'_5$ are not both $C_1$—$_7$ alkyl.

2. A compound according to claim 1 where m is 0.

3. A compound according to claim 2 where $R_{24}$ and $R_{25}$ are hydrogen; $R_{18a}$ is hydrogen, $C_1-C_7$ alkyl, $C_1-C_8$ alkoxymethyl, $C_2-C_8$ alkenyl or benzyl; and the broken line represents a double bond between carbons 24 and 25.

4. A compound according to claim 1 where W is S and n is 0.

5. A compound according to claim 4 where m is 0; $R_{24}$ and $R_{25}$ are hydrogen; $R_{18a}$ is hydrogen, $C_1-C_7$ alkyl, $C_1-C_8$ alkoxymethyl, $C_2-C_8$ alkenyl or benzyl; and the broken line represents a double bond between carbons 24 and 25.

6. A compound according to claim 5 which is selected from 18-thiomarcfortine A;
1-acetoxymethyl-18-thiomarcfortine A;
1-diethoxyphosphoryl-18-thiomarcfortine A;
1-dimethylsulfamoyl-18-thiomarcfortine A;
1-cyclopropylcarbonyl-18-thiomarcfortine A;
1-(1-piperidinyl)thiocarbonyl-18-thiomarcfortine A;
1-succinoyl-18-thiomarcfortine A;
1-(2,4-dinitrobenzenesulfenyl)-18-thiomarcfortine A;
1-(4-morpholinosulfenyl)-18-thiomarcfortine A;
24-propoxy-24,25-dihydro-18-thiomarcfortine A;
1-(p-toluenesulfonyl)-18-thiomarcfortine A;
1-acetyl-18-thiomarcfortine A;
1-methyl-18-thiomarcfortine A;
1-benzyl-18-thiomarcfortine A;
1-dimethylcarbamoyl-18-thiomarcfortine A;
1-methoxycarbonyl-18-thiomarcfortine A;
18-thiomarcfortine B;
24,25-dihydro-18-thiomarcfortine B;
24-methoxy-24,25-dihydro-18-thiomarcfortine B;
1-(p-toluenesulfonyl)-18-thiomarcfortine B;
1-acetyl-18-thiomarcfortine B;
1-ethyl-18-thiomarcfortine B;
1-benzyl-18-thiomarcfortine B;
18a-ethyl-18-thiomarcfortine B;
18a-benzyl-18-thiomarcfortine B;
18a-methoxyethoxymethyl-18-thiomarcfortine B;
18a-allyl-18-thiomarcfortine B;
18a-propargyl-18-thiomarcfortine B;
18a-ethyl-24-methoxy-24,25-dihydro-18-thiomarcfortine B;
18 ethyl-18-benzyl-18-thiomarcfortine B;
18a-ethyl-24-methoxy-18-thiomarcfortine B;
1-(2,4-dinitrobenzene sulfonyl)-18a-ethyl-24-methoxy-24,25-dihydro-18-thiomarcfortine B;
18a-ethyl-24,25 dihydro-18-thiomarcfortine B;
18-thiomarcfortine C;
24,25 dihydro-18-thiomarcfortine C;
1-(p-bromobenzene sulfonyl)-18-thiomarcfortine C;
1-propionyl-18-thiomarcfortine C;
1-propyl-18-thiomarcfortine C;
1-benzyl-18-thiomarcfortine C;
18a-propyl-18-thiomarcfortine C;
18a-benzyl-18-thiomarcfortine C;
18a-methoxyethoxymethyl-18-thiomarcfortine C;
18a-allyl-18-thiomarcfortine C;
18a-propargyl-18-propyl-18-benzyl-18-thiomarcfortine C;
1-(4-carbethoxy-1,3-thiazolidinin-3-yl)carbonyl-18-thiomarcfortine A;
1-palmitoyl-18-thiomarcfortine A; and 1-(4-morpholinocarbonyl)-18-thiomarcfortine A.

7. A compound according to claim 1 where W is S and n is 1.

8. A compound according to claim 7 where m is 0; $R_{24}$ and $R_{25}$ are hydrogen; $R_{18a}$ is hydrogen, $C_1$–$C_7$ alkyl, $C_1$–$C_8$ alkoxymethyl, $C_2$–$C_8$ alkenyl or benzyl; and the broken line represents a double bond between carbons 24 and 25.

9. A compound according to claim 8 where $R_{14a}$ and $R_{14b}$ are both hydrogen.

10. A compound according to claim 8 where $R_{14a}$ is methyl, $R_{14b}$ is hydroxy.

11. A compound according to claim 8 which is selected from 18-thioparaherquamide
24,25-dihydro-18-thioparaherquamide
14-O-methyl-18-thioparaherquamide
14-O-ethyl-18-thioparaherquamide
14-O-butyl-18-thioparaherquamide
14-O-benzyl-18-thioparaherquamide
14-O-allyl-18-thioparaherquamide
14-O-propargyl-18-thioparaherquamide
14-O-methoxymethyl-18-thioparaherquamide
14-O-methoxy-ethoxy-18-thioparaherquamide
14-O-methoxy-ethyoxy-methyl-18-thioparaherquamide
17-methyl-18-thioparaherquamide
17-methylene-18-thioparaherquamide
1-N-(p-toluenesulfonyl)-18-thioparaherquamide and
24-methoxy-24,25-dihydro-18-thioparaherquamide.

12. A compound according to claim 1 wherein W is O and n is 0.

13. A compound according to claim 12 where m is 0; $R_{24}$ and $R_{25}$ are hydrogen; $R_{18a}$ is hydrogen, $C_1$–$C_7$ alkyl, $C_1$–$C_8$ alkoxymethyl, $C_2$–$C_8$ alkenyl or benzyl; and the broken line represents a double bond between carbons 24 and 25.

14. A compound according to claim 1 which is selected from 1-(1-piperidinyl)thiocarbonyl-marcfortine C;
1-(1-piperidinyl)thiocarbonyl-marcfortine A;
1-(2,4-dichlorophenoxy)carbonyl-18a-N-ethyl-24-methoxy-24,25-dihydro-marcfortine B;
1-(2,4-dichlorophenoxycarbonyl)-18a-allyl-marcfortine B;
1-(2,4-dinitrobenzenesulfenyl)-marcfortine A;
1-(3-acetoxy)propionyl-18a-N-propargyl-marcfortine B;
1-(4-carbethoxy-1,3-thiazolidine-3-yl)carbonyl-marcfortine A;
1-(4-morpholinosulfenyl)-marcfortine C;
1-(4-oxobutyryl)-18a-methyl-marcfortine C;
1-(4-oxopentanoyl)-marcfortine A;
1-(4-oxopentanoyl)-marcfortine C;
1-3,4-dichlorobenzoyloxy-marcfortine C;
1-acetoxymethyl marcfortine C;
1-acetoxymethyl-18a-benzyl-marcfortine B;
1-benzoyloxymethyl-marcfortine A;
1-cyclohexylcarbonyl-marcfortine A;
1-cyclohexylcarbonyl-marcfortine C;
1-cyclopropylcarbonyl-marcfortine A;
1-cyclopropylcarbonyl-18a-ethyl-marcfortine B;
1-cyclopropylcarbonyl-marcfortine C;
1-diethoxyphosphoryl-marcfortine A;
1-diethoxythiophosphoryl-marcfortine A;
1-diethoxythiophosphoryl-marcfortine C;
1-dimethylaminoacetyl-marcfortine C;
1-dimethylaminoacetyl-marcfortine A;
1-dimethylaminosulfenyl-18a-N-benzyl-marcfortine B;
1-diphenylphosphinyl-18a-N-allyl-marcfortine B;
1-ethoxycarbonylsulfenyl-18a-methyl-marcfortine C;
1-ethoxycarbonylsulfenyl-18a-N-methoxyethoxymethyl-marcfortine B;
1-N-(2,4-dinitrobenzenesulfenyl)-18a-N-ethyl-marcfortine B;
1-N-(4-carbethoxy-1,3-thiazolidinin-3-yl)carbonyl-marcfortine C;
1-N-(4-carbethoxy-1,3-thiazolidinin-3-yl)carbonyl-marcfortine A;
1-N-(p-bromobenzenesulfenyl)-marcfortine C;
1-N,N-dimethylsuccinamidoyl-marcfortine A;
1-N,N-dimethylsuccinamidoyl-marcfortine C;
1-phenoxycarbonyl-marcfortine C;
1-phenylmethoxyphosphonyl-marcfortine A;
1-phenylmethoxyphosphonyl-marcfortine C;
1-succinoyl-marcfortine A;
1-succinoyl-marcfortine C;
1-t-butyryloxymethyl-marcfortine A; and
1-trichloromethylsulfenyl-18a-ethyl-marcfortine B.

15. A compound according to claim 1 selected from 1-cyclopropylcarbonyl-marcfortine A
1-phenoxycarbonyl-marcfortine A
1-palmitoyl-marcfortine A
1-[[(4-nitrophenyl)oxy]carbonyl]-marcfortine A
1-(1-piperidinecarbonyl)-marcfortine A
1-[[4-(ethoxycarbonyl)piperazin-1-yl]carbonyl]-marcfortine A
1-[[4-(benzyl)piperazin-1-yl]carbonyl]-marcfortine A
1-[[4-(1,3-benzodioxol-5-yl-methyl)piperazin-1-yl]carbonyl]-marcfortine A
1-[[4-(methyl)piperazin-1-yl]carbonyl]-marcfortine A
1-(1,3-dihydro-1,3-dioxo-2H-isoindol-2-yl)-marcfortine A
1-[[4-(pyridin-2-yl)piperazin-1-yl]carbonyl]-marcfortine A
1-[[4-(phenyl)piperazin-1-yl]carbonyl]-marcfortine A
1-[[4-(chlorocarbonyl)piperazin-1-yl]carbonyl]-marcfortine A
1-[[4-(phenyl)piperidin-1-yl]carbonyl]-marcfortine A
1-[[4-(phenyl)(dimethyl)piperidin-1-yl]carbonyl]-marcfortine A
1-[[4-(5-chloropyridazin-3-yl)piperazin-1-yl]carbonyl]-marcfortine A
1-[[4-(4-chlorophenyl)piperazin-1-yl]carbonyl]-marcfortine A
1-[[4-(trichloroethoxycarbonyl)piperazin-1-yl]carbonyl]-marcfortine A
1-[[4-(3-trifluoromethyl-thiadiazol-1-yl)piperazin-1-yl]carbonyl]-marcfortine-A
1-acetoxymethyl-marcfortine A
1-(2,4-dinitrobenzenesulfenyl)-marcfortine A
1-(4-morpholinosulfenyl)-marcfortine A
1-(trichloromethylsulfenyl)-marcfortine A 1-(methoxycarbonylsulfenyl)-marcfortine A
1-(benzenesulfenyl)-marcfortine A
1-(2-tetrahydrofuranyl)-marcfortine A,
1-(4-morpholinocarbonyl)-marcfortine A and
1-(4-morpholinocarbonyl)-marcfortine A N-oxide.

16. A compound according to claim 1 selected from 1-diethoxyphosphoryl-paraherquamide
1-cyclopropylcarbonyl-paraherquamide
1-(1-piperidinyl)thiocarbonyl-paraherquamide
1-succinoyl-paraherquamide
1-(4-carbethoxy-1,3-thiazolidinin-3-yl)carbonyl-paraherquamicde
1-phenoxycarbonyl-paraherquamide
1-pyrrolidinylcarbonyl-paraherquamide
1-t-butyryloxymethyl-paraherquamide
1-benzoyloxymethyl-paraherquamide
1-acetoxymethyl-18a-paraherquamide
1-3,4-dichlorobenzoyloxy-paraherquamide
1-(2,4-dinitrobenzenesulfenyl)-paraherquamide
b 1-(4-morpholinosulfenyl)-paraherquamide
1-trichloromethylsulfenyl-18a-ethyl-paraherquamide
1-ethoxycarbonylsulfenyl-18a-methyl-paraherquamide
1-palmitoyl-paraherquamide
1-piperidinylcarbonyl-paraherquamide and
1-(4-morpholinecarbonyl)-paraherquamide.

17. A compound according to claim 1 where $R'_4$ and $R'_5$ are taken together with N, to form a saturated heterocyclic amine ring selected from the group consisting of 4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine thiazolidine,
4-phenyl-1,2,3,6-tetrahydropyridine,
4-phenylpiperidine,
ethyl prolinate,
tetrahydrofurylamine,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine or
N-carboethoxypiperazine.

18. A compound selected from the group consisting of
10,10"-(1,4-dicarbonylpiperazine)bis(6',7',8',9',10',10'a-hexahydro-1',1',4,4,12'-pentamethyl)-[2'S-[2'.alpha., 3'a.alpha.,9'a.alpha, 10(2'"R*,3'"aS*9"'aS*, 10'"aR*), 10'a.beta.]]-Spiro[4H,8H-[1,4]dioxepino[2,3-g]indole-8,2'(3'H)-[1H,4H-3a,9a](iminomethano) cyclopenta[b] quinolizin]-9,11'(10H)-dione; or 10,10"-(1,4-dioxo-2-butene)bis(6',7',8',9',10',10'a-hexahydro-1',1',4,4,12'-pentamethyl)-[2'S-[2'.alpha., 3'a.alpha.9'a alpha,10(2'"R*,3'"aS*9"'aS*, '"aR*), 10'a.beta]]-Spiro[4H,8H-[1,4]dioxepino[2,3-g]indole-8,2'(3'H)-[1H,4H-3a,9a](iminomethano)cyclopenta[b] quinolizin]-9,11'(10H)-dione.

19. A method for the treatment or prevention of helminth or arthropod infections in domesticated animals which comprises treating such animals with an effective amount of a compound of Formula I

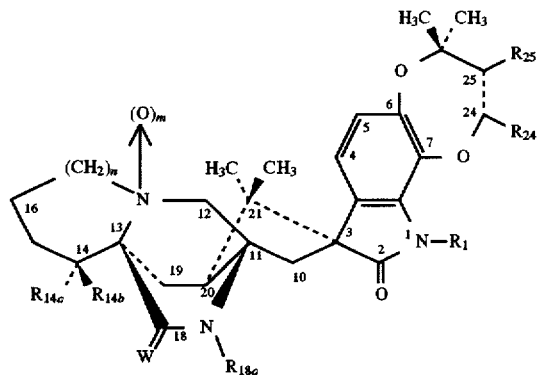

wherein:

n is 0 or 1;

$R_{14a}$ and $R_{14b}$, being the same or different, are selected from hydrogen, hydroxy, $C_1$–$C_6$ alkyl, $C_1$–$C_6$ alkoxy, $C_1$–$C_6$ alkenyl, $C_1$–$C_6$ alkenyl–$C_1$–$C_6$ alkoxy, $C_1$–$C_6$ alkynyl-$C_1$–$C_6$ alkoxy, $C_1$–$C_6$ alkynoyloxy, poly $C_1$–$C_6$ alkoxy–$C_1$–$C_6$ alkoxy, phenyl, phenyl-$C_1$–$C_6$ alkyl, tri-$C_1$–$C_6$ alkylsilyloxy, diphenylphosphoryloxy and halogen, or $R_{14a}$ and $R_{14b}$ together form the epoxide or =$CH_2$, with the provisio that when n is 1, then $R_{14a}$ and $R_{14b}$ are both hydrogen;

m is 0 or 1;

W is O or S;

when W is S, $R_1$ is hydrogen, $C_1$–$C_7$ alkyl, cyclo $C_1$–$C_8$alkyl, benzyl, $C_2$–$C_7$ alkanoyl (—C(O) $C_1$–$C_6$alkyl), $C_1O$–$C_{24}$alkanoyl (—C(O)$C_1$–$C_{23}$alkyl cyclo $C_3$–$C_8$alkanoyl, $C_{10}$–$C_{24}$alkenoyl (—C(O) $C_1$–$C_{23}$alkenyl), benzenesulfonyl (—$SO_2$phenyl), di($C_1$–$C_4$alkyl)aminocarbonyl (—C(O)N($C_1$–$C_4$alkyl)$_2$), di($C_1$–$C_4$alkyl)aminothiocarbonyl (—C(S)N ($C_1$–$C_4$alkyl)$_2$), $C_1$–$C_7$ alkoxycarbonyl, phenoxycarbonyl, —C(O)NR'$_4$R'$_5$, —P(=X)($R_2$)($R_3$), —$SR_6$, —$SO_2NR_4R_5$, benzoyl substituted at the 3 or 4 position with —$CH_2NR_4R_5$, 2-tetrahydrofuran, or bicycloC$_8$–$C_{12}$alkanoyl;

when W is O; $R_1$ is selected from the group consisting of:

(a) $C_2$–$C_7$ alkanoyl substituted with carboxy (—COOH), $C_1$–$C_7$ alkenoyl, carbo$C_1$–$C_7$alkoxy (—C(O)O$C_1$–$C_7$alkyl), —$NR_4R_5$, aminocarbonyl (—C(O)$NR_4R_5$);

(b) cyclo $C_1$–$C_8$alkanoyl optionally substituted with carboxy, $C_1$–$C_7$ alkanoyl, carbo$C_1$–$C_7$alkoxy, —$NR_4R_5$, aminocarbonyl;

(c) alkanoyloxymethylene (—$CH_2OC(O)$ –$C_2$–$C_7$alkyl);

(d) benzoyloxymethlene (—$CH_2OC(O)$phenyl) substituted with 1 or 2 groups selected from halogen, $C_1$–$C_4$ alkyl, halo$C_1$–$C_7$alkyl, nitro, cyano and $C_1$–$C_7$alkoxy;

(e) phenoxycarbonyl substituted with 1 or 2 groups selected from halogen, $C_1$–$C_4$ alkyl, halo$C_1$–$C_7$alkyl, nitro, cyano and $C_1$–$C_7$alkoxy;

(f) —C(O)NR'$_4$R'$_5$;
(g) —O(=X)(R$_2$)(R$_3$);
(h) —SR$_6$;
(i) C$_1$–C$_{24}$alkanoyl (—C(O)C$_{10}$–C$_{24}$alkyl);
(j) C$_{10}$–C$_{24}$alkenoyl (—C(O)C$_1$–C$_{23}$alkenyl); or
(k) 2-tetrahydrofuran;

R$_4$ and R$_5$, being the same or different, are selected from hydrogen, C$_1$–C$_7$ alkyl, phenyl or when taken together with N, form a saturated or unsaturated heterocyclic amine ring selected from the group consisting of:

4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine thiazolidine,
4-phenyl-1,2,3,6-tetrahydropyridine,
4-phenylpiperidine,
ethyl prolinate,
tetrahydrofurylamine,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine and
N-carboethoxypiperazine;

R'$_4$ and R'$_5$, being the same or different, are selected from C$_1$–C$_7$ alkyl, cyclo(C$_3$–C$_8$)alkyl, phenyl or when taken together with N, form a saturated heterocyclic amine ring selected from the group consisting of 4-morpholine,
4-phenyl-1-piperazine,
4-(2-pyridinyl)-1-piperazine,
2,6-dimethyl-4-morpholine,
1-pyrrolidine,
4-methyl-1-piperazine,
1-piperidine,
4-phenyl-1-piperidine
thiazolidine,
4-phenyl-1,2,3,6-tetrahydropyridine,
4-phenylpiperidine,
ethyl prolinate,
tetrahydrofurylamine,
3-pyrroline,
thiazolidine-4-carboxylic acid,
thiomorpholine,
nipecotamide,
2-methylpiperidine,
3-methylpiperidine,
4-methylpiperidine,
N-methylpiperazine,
1-methylhomopiperazine,
1-acetylpiperazine and
N-carboethoxypiperazine;

X is O or S;

R$_2$ and R$_3$, being the same or different, are selected from C$_1$–C$_7$ alkyl, phenyl, C$_1$–C$_7$ alkoxy, thio(C$_1$–C$_7$)alkoxy, phenoxy, thiophenoxy, —NR$_7$R$_8$, or taken together with P form a 4- to 7-membered heterocyclic ring selected from the group consisting of 1,3-dioxa-2-phosphorinane, 1-aza-3-oxa- 2-phospholane, 1,3-diaza-2-phospholane and 1-thia-3-oxa-2-phospholane;

R$_6$ is C$_1$–C$_7$ alkyl, haloC$_1$–C$_7$alkyl, carboC$_1$–C$_7$alkoxy, —NR$_9$R$_{10}$ where R$_9$ and R$_{10}$, being the same or different, are C$_1$–C$_7$ alkyl or phenyl (optionally substituted with 1 or 2 groups selected from halo, lower alkyl, haloC$_1$–C$_7$alkyl, nitro, cyano, C$_1$–C$_7$ alkoxy);

R$_{24}$ is hydrogen, halogen or C$_1$–C$_7$ alkoxy;

R$_{25}$ is hydrogen or halogen;

R$_{18a}$ is hydrogen, C$_1$–C$_7$ alkyl, C$_2$–C$_8$ alkoxyalkyl, C$_2$–C$_8$ alkenyl, C$_2$–C$_8$ alkynyl or benzyl;

the broken line between carbons 24 and 25 represents a single or double bond; and pharmaceutically acceptable salts and hydrates thereof; with the overall proviso that, when W is O, R'$_4$ and R'$_5$ are not both C$_{1-7}$ alkyl.

* * * * *